US006797483B1

(12) United States Patent
Itoh et al.

(10) Patent No.: US 6,797,483 B1
(45) Date of Patent: Sep. 28, 2004

(54) POLYPEPTIDE AND DNA THEREOF

(75) Inventors: Yasuaki Itoh, Ibaraki (JP); Kazunori Nishi, London (GB); Kazuhiro Ogi, Ibaraki (JP); Shoichi Ohkubo, Ibaraki (JP); Shinichi Mogi, Ibaraki (JP); Yuko Noguchi, Ibaraki (JP); Koji Yoshimura, Ibaraki (JP); Hideyuki Tanaka, Ibaraki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 8 days.

(21) Appl. No.: 10/019,455
(22) PCT Filed: Jun. 29, 2000
(86) PCT No.: PCT/JP00/04278
§ 371 (c)(1),
(2), (4) Date: Dec. 28, 2001
(87) PCT Pub. No.: WO01/02564
PCT Pub. Date: Jan. 11, 2001

(30) Foreign Application Priority Data

Jun. 30, 1999 (JP) .......................................... 11/186718

(51) Int. Cl.$^7$ ......................... G01N 33/53; C12P 21/06; C12N 15/87; C12N 1/20; C12N 15/74; C07H 21/04; C07K 14/00; C07K 17/08
(52) U.S. Cl. ....................... 435/7.1; 435/69.1; 435/455; 435/325; 435/252.3; 435/320.1; 530/350; 530/391.1; 536/23.5
(58) Field of Search ........................ 536/23.5; 435/69.1, 435/7.1, 455, 252.3, 320.1; 530/350, 399, 391.1; 424/184.1, 185.1

(56) References Cited

U.S. PATENT DOCUMENTS 5,770,366 A    6/1998  Bogdahn et al.

FOREIGN PATENT DOCUMENTS

| US | WO 99/32614 | 1/1999 |
| WO | WO 98/31800 | 7/1998 |
| WO | WO 01/48203 | 7/2001 |
| WO | WO 01/55332 | 8/2001 |

OTHER PUBLICATIONS

Burgess, et al. Possible dissociation of the heparin–binding and mitogenic activities of heparin–binding growth factor–1 from its receptor–binding activities by site–directed mutagenesis of a single lysine residue. J Cell Biol. 111:2129–2138, 1990.*
Bowie JU, et al Deciphering the message in protein sequences: tolerance to amino acid substitutions. Science. 247(4948):1306–1310, 1990.*
Lazar E et al., Transforming growth factor alpha: mutation of aspartic acid 47 and leucine 48 results in different biological activities. Mol Cell Biol. 8:1247–1252, 1988.*

Attwood TK. Genomics. The Babel of bioinformatics. Science. 290(5491):471–473, 2000.*
Skolnick et al. From genes to protein structure and function: novel applications of computational approaches in the genomic era. Trends Biotechnol. 18(1):34–9, 2000.*
Metzler et al . Solution structure of human CTLA–4 and delineation of a CD80/CD86 binding site conserved in CD28. Nat Struc Biol. 4(7):527–531, 1997.*
Ngo J.T, Marks J., Karplus M., Computational complexity, protein structure prediction, and the Levinthal paradox in The Protein Folding Problem, ch.14, pp. 435–508, Birkhauser, 1994.*
Dietz, et al *"Cloning of a Retinoic Acid–Sensitive mRNA Expressed in Cartilage and During Chondrogeneis"*, The Journal of Biological Chemistry, vol. 271, No. 6, Issue of Feb. 9, 1996, pp. 3311–3316.
Xiet, et al *"Regulation of the Mouse Cartilage–Derived Retinoic Acid–Sensitive Protein Gene by the Transcription Factor AP–2"*, The Journal of Biological Chemistry, vol. 273, No. 9, Issue of Feb. 27, 1998, pp. 5206–5032.
Bosserhoff, et al *"Structure and Promoter Analysis of the Gene Encoding the Human Melanoma–Inhibiting Protein MIA"*, The Journal of Biological Chemistry, vol. 271, No. 1, Issue of Jan. 5, 1996, pp. 490–495.
Blesch, et al *"Cloning of a Novel Malignant Melanoma–Derived–Regulatory Protein, MIA"*, Cancer Research, vol. 54, Issue orf Nov. 1, 1994, pp. 5695–5701.
Database EMBL, 'Online!, Feb. 20, 1997, Marra et al., "The WahU–HHMI mouse EST project", AA222797 XP002199700.
Database EMBL Online! Jun. 28, 1999, Arakawa et al., AV169321 XP002199699.
Bosserhoff et al, Mouse CD–RAP/MIA gene: Structure, Chromosomal Localization, and Expression in Cartilage and Chondrosarcoma, Developmental Dynamics 208: 516–525 (1997).

* cited by examiner

*Primary Examiner*—Christina Chan
*Assistant Examiner*—Maher Haddad
(74) *Attorney, Agent, or Firm*—David G. Conlin; Christine C. O'Day; Edwards & Angell, LLP

(57) ABSTRACT

The present invention relates to novel secretory polypeptides and precursor proteins thereof, which show a high homology to MIA (melanoma inhibitor activity)/CD-RAP (bovine cartilage-derived retinoic acid-sensitive protein); are specifically expressed in the cartilage tissue; and have an effect on the cartilage differentiation. The polypeptides and the DNAs encoding the same can be used for the diagnosis, treatment, or prevention of bone and joint diseases or pathological angiogenesis. As well, the polypeptides are useful as a reagent for screening a compound that promotes or inhibits the activity of the polypeptides. The antibody to the polypeptides can be used for the detection, quantification, or neutralization of the polypeptide in a test sample fluid. Further by using the promoter of the present invention, a therapeutic protein can be expressed predominantly in the cartilage tissue for a gene therapy.

18 Claims, 4 Drawing Sheets

Fig. 1

SEQUENCE LISTING

<160> NUMBER OF SEQ ID NOS: 53

<210> SEQ ID NO 1
<211> LENGTH: 26
<212> TYPE: DNA
<213> ORGANISM: Artificial Sequence -continued

```
<220> FEATURE:
<223> OTHER INFORMATION: Description of Artificial Sequence: Primer

<400> SEQUENCE: 1
cgcagaagaa gtcaatatcc gtggtg                                              26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 2
cagcgtgtgt accaggaagc taccaa                                              26

<210> SEQ ID NO 3
<211> LENGTH: 131
<212> TYPE: PRT
<213> ORGANISM: Homo sapiens

<400> SEQUENCE: 3

Met Ala Arg Ser Leu Val Cys Leu Gly Val Ile Ile Leu Leu Ser Ala
  1               5                  10                  15

Phe Ser Gly Pro Gly Val Arg Gly Gly Pro Met Pro Lys Leu Ala Asp
                 20                  25                  30

Arg Lys Leu Cys Ala Asp Gln Glu Cys Ser His Pro Ile Ser Met Ala
             35                  40                  45

Val Ala Leu Gln Asp Tyr Met Ala Pro Asp Cys Arg Phe Leu Thr Ile
         50                  55                  60

His Arg Gly Gln Val Val Tyr Val Phe Ser Lys Leu Lys Gly Arg Gly
 65                  70                  75                  80

Arg Leu Phe Trp Gly Gly Ser Val Gln Gly Asp Tyr Tyr Gly Asp Leu
                 85                  90                  95

Ala Ala Arg Leu Gly Tyr Phe Pro Ser Ser Ile Val Arg Glu Asp Gln
            100                 105                 110

Thr Leu Lys Pro Gly Lys Val Asp Val Lys Thr Asp Lys Trp Asp Phe
            115                 120                 125

Tyr Cys Gln
        130

<210> SEQ ID NO 4
<211> LENGTH: 384
<212> TYPE: DNA
<213> ORGANISM: Homo sapiens
<220> FEATURE:
<221> NAME/KEY: CDS
<222> LOCATION: (1)..(384)

<400> SEQUENCE: 4 atg gca aga ata ttg tta ctt ttc ctc ccg ggt ctt gtg gct gta tgt      48
Met Ala Arg Ile Leu Leu Leu Phe Leu Pro Gly Leu Val Ala Val Cys
  1               5                  10                  15 gct gtg cat gga ata ttt atg gac cgt cta gct tcc aag aag ctc tgt      96
Ala Val His Gly Ile Phe Met Asp Arg Leu Ala Ser Lys Lys Leu Cys
                 20                  25                  30 gca gat gat gag tgt gtc tat act att tct ctg gct agt gct caa gaa     144
Ala Asp Asp Glu Cys Val Tyr Thr Ile Ser Leu Ala Ser Ala Gln Glu
             35                  40                  45
```

-continued

```
gat tat aat gcc ccg gac tgt aga ttc att aac gtt aaa aaa ggg cag      192
Asp Tyr Asn Ala Pro Asp Cys Arg Phe Ile Asn Val Lys Lys Gly Gln
     50                  55                  60 cag atc tat gtg tac tca aag ctg gta aaa gaa aat gga gct gga gaa      240
Gln Ile Tyr Val Tyr Ser Lys Leu Val Lys Glu Asn Gly Ala Gly Glu
 65                  70                  75                  80 ttt tgg gct ggc agt gtt tat ggt gat ggc cag gac gag atg gga gtc     288
Phe Trp Ala Gly Ser Val Tyr Gly Asp Gly Gln Asp Glu Met Gly Val
                 85                  90                  95 gtg ggt tat ttc ccc agg aac ttg gtc aag gaa cag cgt gtg tac cag     336
Val Gly Tyr Phe Pro Arg Asn Leu Val Lys Glu Gln Arg Val Tyr Gln
             100                 105                 110 gaa gct acc aag gaa gtt ccc acc acg gat att gac ttc ttc tgc gag     384
Glu Ala Thr Lys Glu Val Pro Thr Thr Asp Ile Asp Phe Phe Cys Glu
         115                 120                 125
```

<210> SEQ ID NO 5
<211> LENGTH: 18
<212> TYPE: PRT
<213> ORGANISM: Homo sapiens

<400> SEQUENCE: 5

Met Ala Arg Ile Leu Leu Leu Phe Leu Pro Gly Leu Val Ala Val Cys
 1               5                  10                  15

Ala Val

<210> SEQ ID NO 6
<211> LENGTH: 128
<212> TYPE: PRT
<213> ORGANISM: Homo sapiens

<400> SEQUENCE: 6

Met Ala Arg Ile Leu Leu Leu Phe Leu Pro Gly Leu Val Ala Val Cys
 1               5                  10                  15

Ala Val His Gly Ile Phe Met Asp Arg Leu Ala Ser Lys Lys Leu Cys
                 20                  25                  30

Ala Asp Asp Glu Cys Val Tyr Thr Ile Ser Leu Ala Ser Ala Gln Glu
             35                  40                  45

Asp Tyr Asn Ala Pro Asp Cys Arg Phe Ile Asn Val Lys Lys Gly Gln
     50                  55                  60

Gln Ile Tyr Val Tyr Ser Lys Leu Val Lys Glu Asn Gly Ala Gly Glu
 65                  70                  75                  80

Phe Trp Ala Gly Ser Val Tyr Gly Asp Gly Gln Asp Glu Met Gly Val
                 85                  90                  95

Val Gly Tyr Phe Pro Arg Asn Leu Val Lys Glu Gln Arg Val Tyr Gln
             100                 105                 110

Glu Ala Thr Lys Glu Val Pro Thr Thr Asp Ile Asp Phe Phe Cys Glu
         115                 120                 125

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
cacacagcac gtagtcgcag ttgg                                            24

-continued

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
aacttggtga aggagcagcg tgta                                            24

<210> SEQ ID NO 9
<211> LENGTH: 130
<212> TYPE: PRT
<213> ORGANISM: Mus sp.

<400> SEQUENCE: 9

Met Val Trp Ser Pro Val Leu Leu Gly Ile Val Val Leu Ser Val Phe
 1               5                  10                  15

Ser Gly Pro Ser Arg Ala Asp Arg Ala Met Pro Lys Leu Ala Asp Trp
            20                  25                  30

Lys Leu Cys Ala Asp Glu Glu Cys Ser His Pro Ile Ser Met Ala Val
        35                  40                  45

Ala Leu Gln Asp Tyr Val Ala Pro Asp Cys Arg Phe Leu Thr Ile Tyr
    50                  55                  60

Arg Gly Gln Val Val Tyr Val Phe Ser Lys Leu Lys Gly Arg Gly Arg
65                  70                  75                  80

Leu Phe Trp Gly Gly Ser Val Gln Gly Tyr Tyr Gly Asp Leu Ala
                85                  90                  95

Ala Arg Leu Gly Tyr Phe Pro Ser Ser Ile Val Arg Glu Asp Leu Thr
            100                 105                 110

Leu Lys Pro Gly Lys Ile Asp Met Lys Thr Asp Gln Trp Asp Phe Tyr
        115                 120                 125

Cys Gln
    130

<210> SEQ ID NO 10
<211> LENGTH: 384
<212> TYPE: DNA
<213> ORGANISM: Mus sp.
<220> FEATURE:
<221> NAME/KEY: CDS
<222> LOCATION: (1)..(384)

<400> SEQUENCE: 10 atg gca agg ata ttg att ctt ttg ctt ggg ggc ctt gtg gtt cta tgt      48
Met Ala Arg Ile Leu Ile Leu Leu Leu Gly Gly Leu Val Val Leu Cys
 1               5                  10                  15 gcc ggg cat ggt gta ttt atg gat aaa ctt tct tct aag aag ttg tgt      96
Ala Gly His Gly Val Phe Met Asp Lys Leu Ser Ser Lys Lys Leu Cys
            20                  25                  30 gcg gat gag gag tgt gtc tat act att tct ctg gca aga gca cag gaa     144
Ala Asp Glu Glu Cys Val Tyr Thr Ile Ser Leu Ala Arg Ala Gln Glu
        35                  40                  45 gat tac aat gcc cca gac tgt agg ttc atc gat gtc aag aaa ggg cag     192
Asp Tyr Asn Ala Pro Asp Cys Arg Phe Ile Asp Val Lys Lys Gly Gln
    50                  55                  60 cag atc tat gtt tac tcc aag ctg gta aca gaa aac gga gct gga gag     240
Gln Ile Tyr Val Tyr Ser Lys Leu Val Thr Glu Asn Gly Ala Gly Glu
65                  70                  75                  80

```
ttt tgg gct ggc agt gtt tat ggt gac cac cag gat gag atg gga att   288
Phe Trp Ala Gly Ser Val Tyr Gly Asp His Gln Asp Glu Met Gly Ile
             85                  90                  95 gta ggt tat ttc ccc agc aac ttg gtg aag gag cag cgt gta tac cag   336
Val Gly Tyr Phe Pro Ser Asn Leu Val Lys Glu Gln Arg Val Tyr Gln
        100                 105                 110 gag gcc acc aag gag atc cca acc acg gat att gac ttc ttc tgt gaa   384
Glu Ala Thr Lys Glu Ile Pro Thr Thr Asp Ile Asp Phe Phe Cys Glu
        115                 120                 125
```

<210> SEQ ID NO 11
<211> LENGTH: 18
<212> TYPE: PRT
<213> ORGANISM: Mus sp.

<400> SEQUENCE: 11

```
Met Ala Arg Ile Leu Ile Leu Leu Leu Gly Gly Leu Val Val Leu Cys
 1               5                  10                  15

Ala Gly
```

<210> SEQ ID NO 12
<211> LENGTH: 128
<212> TYPE: PRT
<213> ORGANISM: Mus sp.

<400> SEQUENCE: 12

```
Met Ala Arg Ile Leu Ile Leu Leu Leu Gly Gly Leu Val Val Leu Cys
 1               5                  10                  15

Ala Gly His Gly Val Phe Met Asp Lys Leu Ser Ser Lys Lys Leu Cys
                20                  25                  30

Ala Asp Glu Glu Cys Val Tyr Thr Ile Ser Leu Ala Arg Ala Gln Glu
            35                  40                  45

Asp Tyr Asn Ala Pro Asp Cys Arg Phe Ile Asp Val Lys Lys Gly Gln
        50                  55                  60

Gln Ile Tyr Val Tyr Ser Lys Leu Val Thr Glu Asn Gly Ala Gly Glu
 65                  70                  75                  80

Phe Trp Ala Gly Ser Val Tyr Gly Asp His Gln Asp Glu Met Gly Ile
                85                  90                  95

Val Gly Tyr Phe Pro Ser Asn Leu Val Lys Glu Gln Arg Val Tyr Gln
            100                 105                 110

Glu Ala Thr Lys Glu Ile Pro Thr Thr Asp Ile Asp Phe Phe Cys Glu
        115                 120                 125
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
accacagtcc atgccatcac                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 14
tccaccaccc tgttgctgta                                              20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctaccgcgtg cgcccatcat caga                                         24

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gggaggccgg tttggttggg gtaga                                        25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cacactggta agtggggcaa gaccg                                        25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggattgtgtt gtttcagggt tcggg                                        25

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
accccctggc ccctctgga                                               19

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 20
atctcacctt tagcccctgg aatg                                          24

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gccgggcatg gtgtatttat                                               20

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gatctccttg gtggcctcct ggtat                                         25

<210> SEQ ID NO 23
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 23 cat gga ata ttt atg gac cgt cta gct tcc aag aag ctc tgt gca gat      48
His Gly Ile Phe Met Asp Arg Leu Ala Ser Lys Lys Leu Cys Ala Asp
 1               5                  10                  15 gat gag tgt gtc tat act att tct ctg gct agt gct caa gaa gat tat      96
Asp Glu Cys Val Tyr Thr Ile Ser Leu Ala Ser Ala Gln Glu Asp Tyr
             20                  25                  30 aat gcc ccg gac tgt aga ttc att aac gtt aaa aaa ggg cag cag atc     144
Asn Ala Pro Asp Cys Arg Phe Ile Asn Val Lys Lys Gly Gln Gln Ile
         35                  40                  45 tat gtg tac tca aag ctg gta aaa gaa aat gga gct gga gaa ttt tgg     192
Tyr Val Tyr Ser Lys Leu Val Lys Glu Asn Gly Ala Gly Glu Phe Trp
     50                  55                  60 gct ggc agt gtt tat ggt gat ggc cag gac gag atg gga gtc gtg ggt     240
Ala Gly Ser Val Tyr Gly Asp Gly Gln Asp Glu Met Gly Val Val Gly
 65                  70                  75                  80 tat ttc ccc agg aac ttg gtc aag gaa cag cgt gtg tac cag gaa gct     288
Tyr Phe Pro Arg Asn Leu Val Lys Glu Gln Arg Val Tyr Gln Glu Ala
                 85                  90                  95 acc aag gaa gtt ccc acc acg gat att gac ttc ttc tgc gag             330
Thr Lys Glu Val Pro Thr Thr Asp Ile Asp Phe Phe Cys Glu
            100                 105                 110

<210> SEQ ID NO 24
<211> LENGTH: 110
<212> TYPE: PRT
<213> ORGANISM: Homo sapiens

<400> SEQUENCE: 24

His Gly Ile Phe Met Asp Arg Leu Ala Ser Lys Lys Leu Cys Ala Asp
 1               5                  10                  15
```

-continued

```
Asp Glu Cys Val Tyr Thr Ile Ser Leu Ala Ser Ala Gln Glu Asp Tyr
            20                  25                  30

Asn Ala Pro Asp Cys Arg Phe Ile Asn Val Lys Lys Gly Gln Gln Ile
        35                  40                  45

Tyr Val Tyr Ser Lys Leu Val Lys Glu Asn Gly Ala Gly Glu Phe Trp
    50                  55                  60

Ala Gly Ser Val Tyr Gly Asp Gly Gln Asp Glu Met Gly Val Val Gly
65                  70                  75                  80

Tyr Phe Pro Arg Asn Leu Val Lys Glu Gln Arg Val Tyr Gln Glu Ala
                85                  90                  95

Thr Lys Glu Val Pro Thr Thr Asp Ile Asp Phe Phe Cys Glu
            100                 105                 110
```

<210> SEQ ID NO 25
<211> LENGTH: 330
<212> TYPE: DNA
<213> ORGANISM: Mus sp.
<220> FEATURE:
<221> NAME/KEY: CDS
<222> LOCATION: (1)..(330)

<400> SEQUENCE: 25

```
cat ggt gta ttt atg gat aaa ctt tct tct aag aag ttg tgt gcg gat      48
His Gly Val Phe Met Asp Lys Leu Ser Ser Lys Lys Leu Cys Ala Asp
 1               5                  10                  15 gag gag tgt gtc tat act att tct ctg gca aga gca cag gaa gat tac      96
Glu Glu Cys Val Tyr Thr Ile Ser Leu Ala Arg Ala Gln Glu Asp Tyr
            20                  25                  30 aat gcc cca gac tgt agg ttc atc gat gtc aag aaa ggg cag cag atc     144
Asn Ala Pro Asp Cys Arg Phe Ile Asp Val Lys Lys Gly Gln Gln Ile
        35                  40                  45 tat gtt tac tcc aag ctg gta aca gaa aac gga gct gga gag ttt tgg     192
Tyr Val Tyr Ser Lys Leu Val Thr Glu Asn Gly Ala Gly Glu Phe Trp
    50                  55                  60 gct ggc agt gtt tat ggt gac cac cag gat gag atg gga att gta ggt     240
Ala Gly Ser Val Tyr Gly Asp His Gln Asp Glu Met Gly Ile Val Gly
65                  70                  75                  80 tat ttc ccc agc aac ttg gtg aag gag cag cgt gta tac cag gag gcc     288
Tyr Phe Pro Ser Asn Leu Val Lys Glu Gln Arg Val Tyr Gln Glu Ala
                85                  90                  95 acc aag gag atc cca acc acg gat att gac ttc ttc tgt gaa             330
Thr Lys Glu Ile Pro Thr Thr Asp Ile Asp Phe Phe Cys Glu
            100                 105                 110
```

<210> SEQ ID NO 26
<211> LENGTH: 110
<212> TYPE: PRT
<213> ORGANISM: Mus sp.

<400> SEQUENCE: 26

```
His Gly Val Phe Met Asp Lys Leu Ser Ser Lys Lys Leu Cys Ala Asp
 1               5                  10                  15

Glu Glu Cys Val Tyr Thr Ile Ser Leu Ala Arg Ala Gln Glu Asp Tyr
            20                  25                  30

Asn Ala Pro Asp Cys Arg Phe Ile Asp Val Lys Lys Gly Gln Gln Ile
        35                  40                  45

Tyr Val Tyr Ser Lys Leu Val Thr Glu Asn Gly Ala Gly Glu Phe Trp
    50                  55                  60

Ala Gly Ser Val Tyr Gly Asp His Gln Asp Glu Met Gly Ile Val Gly
65                  70                  75                  80
```

Tyr Phe Pro Ser Asn Leu Val Lys Glu Gln Arg Val Tyr Gln Glu Ala
              85                  90                  95

Thr Lys Glu Ile Pro Thr Thr Asp Ile Asp Phe Phe Cys Glu
        100                 105                 110

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 27
cgaattccca ccatggcaag gatattgatt cttttgcttg                            40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 28
gtacagtcga cttcacagaa gaagtcaata tccgtggttg                            40

<210> SEQ ID NO 29
<211> LENGTH: 923
<212> TYPE: DNA
<213> ORGANISM: Homo sapiens

<400> SEQUENCE: 29
gtcagagttc aagttaaaac agaaaaaagg aagatggcaa gaatattgtt acttttcctc     60
ccgggtcttg tggctgtatg tgctgtgcat ggaatattta tggaccgtct agcttccaag    120
aagctctgtg cagatgatga gtgtgtctat actatttctc tggctagtgc tcaagaagat    180
tataatgccc cggactgtag attcattaac gttaaaaaag ggcagcagat ctatgtgtac    240
tcaaagctgg taaagaaaaa tggagctgga gaattttggg ctggcagtgt ttatggtgat    300
ggccaggacg agatgggagt cgtgggttat tcccccagga acttggtcaa ggaacagcgt    360
gtgtaccagg aagctaccaa ggaagttccc accacggata ttgacttctt ctgcgagtaa    420
taaattagtt aaaactgcaa atagaaagaa acaccaaaa ataagaaaa gagcaaaagt      480
ggccaaaaaa tgcatgtctg taattttgga ctgacgtttt aagaatttgt taccttacag    540
aagagcaagg gcttaggggt tggaggtggc agataaaaga ggattttcaa ctcaaatctt    600
gtttcctgct ggcctggtct gcccacgagc tagagcgggg aaatgttgag ctcaaatggg    660
taaattgaga ccagaaaatt atttttttcaa cctagagaat ctcctcttac aggggatgc    720
atataacaga tcatgtatgt gtagttattt ctaagtagta attcttccca gctctttgat    780
ttgccatata taaataggt gggtcgtatg tcttcccttt agacatgatg ttttctactc     840
atttgtctct ctggccaatt gaattattaa taaaggtct gtattatcaa agaaaaaaaa     900
aaaaaaaaaa aaaaaaaaa aaa                                             923

<210> SEQ ID NO 30
<211> LENGTH: 947
<212> TYPE: DNA
<213> ORGANISM: Mus sp.

<400> SEQUENCE: 30
aagaaggaag atggcaagga tattgattct tttgcttggg ggccttgtgg ttctatgtgc     60

```
cgggcatggt gtatttatgg ataaactttc ttctaagaag ttgtgtgcgg atgaggagtg      120
tgtctatact atttctctgg caagagcaca ggaagattac aatgcccag actgtaggtt       180 catcgatgtc aagaaagggc agcagatcta tgtttactcc aagctggtaa cagaaaacgg      240
agctggagag ttttgggctg gcagtgttta tggtgaccac caggatgaga tgggaattgt     300
aggttatttc cccagcaact tggtgaagga gcagcgtgta taccaggagg ccaccaagga     360
gatcccaacc acggatattg acttcttctg tgaataagaa attaattaaa acagcagata    420
aaacagaaac accagtgatg aagaagagaa gaagtggaaa taactgaacc tgtgtatccg    480
taccttcctg gctttatttg gtggcaggag gttggagctt gaaggtgcta agatatggaa    540
attgtcaact cagtcttgtt tactcttgcc ccggtctttc caccaactgc gactaagtgc    600
tgtgtgaata atataggtca tttataaccc aatacttagc tttcagcgag gagaatctttt   660 atttactcag tgatgaacat ataaggtgtt ttatctgtag ttatttctaa atggtcattc    720
tccccagctc tgactccatg tccttaagct tgctgagtta gaagtctgac ttttgggtgt    780
gttttctgtt atttgtctct ctggtcatgt gaagtcttaa taatgtatt gtcatgataa     840 cttcctattg ttactttta tatctgatgc ccttggatag aagaatgtta ggtataaaac      900 aagttttgt actcccaaaa aaaaaaaaaa aaaaaaaaa aaaaaaa                    947
```

<210> SEQ ID NO 31
<211> LENGTH: 21
<212> TYPE: PRT
<213> ORGANISM: Mus sp.

<400> SEQUENCE: 31

Val Lys Glu Gln Arg Val Tyr Gln Glu Ala Thr Lys Glu Ile Pro Thr
 1               5                  10                  15

Thr Asp Ile Asp Cys
            20

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 32
gtacagtcga cttattcaca gaagaagtca atatccgtgg t                        41

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 33
cgaattccca ccatggcaag aatattgtta cttttcctc                          39

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 34
gtacagtcga cctcgcagaa gaagtcaata tccgtggt                           38

```
<210> SEQ ID NO 35
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 35
gtacagtcga cttactcgca gaagaagtca atatccgtgg t                 41

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 36
cgaattccca ccatggtgtg gtccccagtg ctcctt                       36

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 37
gtacagtcga cctggcagta gaaatcccat tgatcggt                     38

<210> SEQ ID NO 38
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 38
gtacagtcga cctggcagta gaaatcccat tgatcggt                     38

<210> SEQ ID NO 39
<211> LENGTH: 87
<212> TYPE: PRT
<213> ORGANISM: Rattus sp.

<400> SEQUENCE: 39

Asp Lys Leu Ser Ser Lys Lys Leu Cys Ala Asp Glu Glu Cys Val Tyr
 1               5                  10                  15

Thr Ile Ser Leu Ala Arg Ala Gln Glu Asp Tyr Asn Ala Pro Asp Cys
                20                  25                  30

Arg Phe Ile Asn Val Lys Lys Gly Gln Gln Ile Tyr Val Tyr Ser Lys
            35                  40                  45

Leu Val Thr Glu Asn Gly Ala Gly Ala Phe Trp Ala Gly Ser Val Tyr
        50                  55                  60

Gly Asp His Gln Asp Glu Met Gly Ile Val Gly Tyr Phe Pro Ser Asn
65                  70                  75                  80

Leu Val Arg Glu Gln Arg Val
                85

<210> SEQ ID NO 40
<211> LENGTH: 261
<212> TYPE: DNA
<213> ORGANISM: Rattus sp.
```

-continued

```
<220> FEATURE:
<221> NAME/KEY: CDS
<222> LOCATION: (2)..(261)

<400> SEQUENCE: 40 g gat aaa ctt tct tct aag aag ttg tgt gca gat gag gag tgt gtc tat      49
  Asp Lys Leu Ser Ser Lys Lys Leu Cys Ala Asp Glu Glu Cys Val Tyr
  1               5                   10                  15 acc att tct ctg gca aga gca cag gaa gac tac aat gcc ccg gac tgt       97
Thr Ile Ser Leu Ala Arg Ala Gln Glu Asp Tyr Asn Ala Pro Asp Cys
            20                  25                  30 agg ttc atc aat gtc aag aaa ggg cag cag atc tat gtt tat tcc aag       145
Arg Phe Ile Asn Val Lys Lys Gly Gln Gln Ile Tyr Val Tyr Ser Lys
        35                  40                  45 ctg gta aca gaa aat gga gct ggg gca ttc tgg gct ggc agt gtt tat       193
Leu Val Thr Glu Asn Gly Ala Gly Ala Phe Trp Ala Gly Ser Val Tyr
    50                  55                  60 ggt gac cac cag gat gag atg gga att gtg ggt tat ttc ccc agc aac       241
Gly Asp His Gln Asp Glu Met Gly Ile Val Gly Tyr Phe Pro Ser Asn
65                  70                  75                  80 ttg gtt aga gag caa cga gt                                             261
Leu Val Arg Glu Gln Arg Val
                85

<210> SEQ ID NO 41
<211> LENGTH: 307
<212> TYPE: DNA
<213> ORGANISM: Rattus sp.
<220> FEATURE:
<221> NAME/KEY: CDS
<222> LOCATION: (22)..(282)

<400> SEQUENCE: 41
gccgggcatg gtgtatttat g gat aaa ctt tct tct aag aag ttg tgt gca       51
                       Asp Lys Leu Ser Ser Lys Lys Leu Cys Ala
                       1               5                   10 gat gag gag tgt gtc tat acc att tct ctg gca aga gca cag gaa gac       99
Asp Glu Glu Cys Val Tyr Thr Ile Ser Leu Ala Arg Ala Gln Glu Asp
            15                  20                  25 tac aat gcc ccg gac tgt agg ttc atc aat gtc aag aaa ggg cag cag       147
Tyr Asn Ala Pro Asp Cys Arg Phe Ile Asn Val Lys Lys Gly Gln Gln
        30                  35                  40 atc tat gtt tat tcc aag ctg gta aca gaa aat gga gct ggg gca ttc       195
Ile Tyr Val Tyr Ser Lys Leu Val Thr Glu Asn Gly Ala Gly Ala Phe
    45                  50                  55 tgg gct ggc agt gtt tat ggt gac cac cag gat gag atg gga att gtg       243
Trp Ala Gly Ser Val Tyr Gly Asp His Gln Asp Glu Met Gly Ile Val
60                  65                  70 ggt tat ttc ccc agc aac ttg gtt aga gag caa cga gta taccaggagg        292
Gly Tyr Phe Pro Ser Asn Leu Val Arg Glu Gln Arg Val
75                  80                  85 gccaccaagg agatc                                                      307

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 42
caccaggatg agatgggaat tgtgggttat                                      30
```

-continued

```
<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 43
gggttatttc cccagcaact tggttagaga                              30

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 44
agacacactc ctcatctgca cacaacttc                               29

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 45
ctcctcatct gcacacaact tcttagaaga                              30

<210> SEQ ID NO 46
<211> LENGTH: 384
<212> TYPE: DNA
<213> ORGANISM: Rattus sp.
<220> FEATURE:
<221> NAME/KEY: CDS
<222> LOCATION: (1)..(384)

<400> SEQUENCE: 46 atg gca aga ata ttg att ctt ttg ctt ggg ggc ctt gtg gct ctc tgt    48
Met Ala Arg Ile Leu Ile Leu Leu Leu Gly Gly Leu Val Ala Leu Cys
 1               5                  10                  15 gcc ggg cat ggc atg ttt atg gat aaa ctt tct tct aag aag ttg tgt    96
Ala Gly His Gly Met Phe Met Asp Lys Leu Ser Ser Lys Lys Leu Cys
             20                  25                  30 gca gat gag gag tgt gtc tat acc att tct ctg gca aga gca cag gaa   144
Ala Asp Glu Glu Cys Val Tyr Thr Ile Ser Leu Ala Arg Ala Gln Glu
         35                  40                  45 gac tac aat gcc ccg gac tgt agg ttc atc aat gtc aag aaa ggg cag   192
Asp Tyr Asn Ala Pro Asp Cys Arg Phe Ile Asn Val Lys Lys Gly Gln
     50                  55                  60 cag atc tat gtt tat tcc aag ctg gta aca gaa aat gga gct ggg gca   240
Gln Ile Tyr Val Tyr Ser Lys Leu Val Thr Glu Asn Gly Ala Gly Ala
 65                  70                  75                  80 ttc tgg gct ggc agt gtt tat ggt gac cac cag gat gag atg gga att   288
Phe Trp Ala Gly Ser Val Tyr Gly Asp His Gln Asp Glu Met Gly Ile
                 85                  90                  95 gtg ggt tat ttc ccc agc aac ttg gtt aga gag caa cga gtg tac cag   336
Val Gly Tyr Phe Pro Ser Asn Leu Val Arg Glu Gln Arg Val Tyr Gln
            100                 105                 110 gag gcc acc aag gag att cca acc acg gat att gac ttc ttc tgt gaa   384
Glu Ala Thr Lys Glu Ile Pro Thr Thr Asp Ile Asp Phe Phe Cys Glu
        115                 120                 125
```

-continued

```
<210> SEQ ID NO 47
<211> LENGTH: 128
<212> TYPE: PRT
<213> ORGANISM: Rattus sp.

<400> SEQUENCE: 47

Met Ala Arg Ile Leu Ile Leu Leu Gly Gly Leu Val Ala Leu Cys
  1               5                  10                  15

Ala Gly His Gly Met Phe Met Asp Lys Leu Ser Ser Lys Lys Leu Cys
             20                  25                  30

Ala Asp Glu Glu Cys Val Tyr Thr Ile Ser Leu Ala Arg Ala Gln Glu
         35                  40                  45

Asp Tyr Asn Ala Pro Asp Cys Arg Phe Ile Asn Val Lys Lys Gly Gln
     50                  55                  60

Gln Ile Tyr Val Tyr Ser Lys Leu Val Thr Glu Asn Gly Ala Gly Ala
 65                  70                  75                  80

Phe Trp Ala Gly Ser Val Tyr Gly Asp His Gln Asp Glu Met Gly Ile
                 85                  90                  95

Val Gly Tyr Phe Pro Ser Asn Leu Val Arg Glu Gln Arg Val Tyr Gln
            100                 105                 110

Glu Ala Thr Lys Glu Ile Pro Thr Thr Asp Ile Asp Phe Phe Cys Glu
        115                 120                 125

<210> SEQ ID NO 48
<211> LENGTH: 330
<212> TYPE: DNA
<213> ORGANISM: Rattus sp.
<220> FEATURE:
<221> NAME/KEY: CDS
<222> LOCATION: (1)..(330)

<400> SEQUENCE: 48 cat ggc atg ttt atg gat aaa ctt tct tct aag aag ttg tgt gca gat      48
His Gly Met Phe Met Asp Lys Leu Ser Ser Lys Lys Leu Cys Ala Asp
  1               5                  10                  15 gag gag tgt gtc tat acc att tct ctg gca aga gca cag gaa gac tac      96
Glu Glu Cys Val Tyr Thr Ile Ser Leu Ala Arg Ala Gln Glu Asp Tyr
             20                  25                  30 aat gcc ccg gac tgt agg ttc atc aat gtc aag aaa ggg cag cag atc     144
Asn Ala Pro Asp Cys Arg Phe Ile Asn Val Lys Lys Gly Gln Gln Ile
         35                  40                  45 tat gtt tat tcc aag ctg gta aca gaa aat gga gct ggg gca ttc tgg     192
Tyr Val Tyr Ser Lys Leu Val Thr Glu Asn Gly Ala Gly Ala Phe Trp
     50                  55                  60 gct ggc agt gtt tat ggt gac cac cag gat gag atg gga att gtg ggt     240
Ala Gly Ser Val Tyr Gly Asp His Gln Asp Glu Met Gly Ile Val Gly
 65                  70                  75                  80 tat ttc ccc agc aac ttg gtt aga gag caa cga gtg tac cag gag gcc     288
Tyr Phe Pro Ser Asn Leu Val Arg Glu Gln Arg Val Tyr Gln Glu Ala
                 85                  90                  95 acc aag gag att cca acc acg gat att gac ttc ttc tgt gaa              330
Thr Lys Glu Ile Pro Thr Thr Asp Ile Asp Phe Phe Cys Glu
            100                 105                 110

<210> SEQ ID NO 49
<211> LENGTH: 110
<212> TYPE: PRT
<213> ORGANISM: Rattus sp.
```

```
<400> SEQUENCE: 49

His Gly Met Phe Met Asp Lys Leu Ser Ser Lys Lys Leu Cys Ala Asp
  1               5                  10                  15

Glu Glu Cys Val Tyr Thr Ile Ser Leu Ala Arg Ala Gln Glu Asp Tyr
             20                  25                  30

Asn Ala Pro Asp Cys Arg Phe Ile Asn Val Lys Lys Gly Gln Gln Ile
         35                  40                  45

Tyr Val Tyr Ser Lys Leu Val Thr Glu Asn Gly Ala Gly Ala Phe Trp
 50                  55                  60

Ala Gly Ser Val Tyr Gly Asp His Gln Asp Glu Met Gly Ile Val Gly
 65                  70                  75                  80

Tyr Phe Pro Ser Asn Leu Val Arg Glu Gln Arg Val Tyr Gln Glu Ala
                 85                  90                  95

Thr Lys Glu Ile Pro Thr Thr Asp Ile Asp Phe Phe Cys Glu
            100                 105                 110

<210> SEQ ID NO 50
<211> LENGTH: 18
<212> TYPE: PRT
<213> ORGANISM: Rattus sp.

<400> SEQUENCE: 50

Met Ala Arg Ile Leu Ile Leu Leu Gly Gly Leu Val Ala Leu Cys
  1               5                  10                  15

Ala Gly

<210> SEQ ID NO 51
<211> LENGTH: 130
<212> TYPE: PRT
<213> ORGANISM: Rattus sp.

<400> SEQUENCE: 51

Met Val Cys Ser Pro Val Leu Leu Gly Ile Val Ile Leu Ser Val Phe
  1               5                  10                  15

Ser Gly Leu Ser Arg Ala Asp Arg Ala Met Pro Lys Leu Ala Asp Arg
             20                  25                  30

Lys Leu Cys Ala Asp Glu Glu Cys Ser His Pro Ile Ser Met Ala Val
         35                  40                  45

Ala Leu Gln Asp Tyr Val Ala Pro Asp Cys Arg Phe Leu Thr Ile Tyr
 50                  55                  60

Arg Gly Gln Val Val Tyr Val Phe Ser Lys Leu Lys Gly Arg Gly Arg
 65                  70                  75                  80

Leu Phe Trp Gly Gly Ser Val Gln Gly Asp Tyr Tyr Gly Asp Leu Ala
                 85                  90                  95

Ala His Leu Gly Tyr Phe Pro Ser Ser Ile Val Arg Glu Asp Leu Thr
            100                 105                 110

Leu Lys Pro Gly Lys Val Asp Met Lys Thr Asp Glu Trp Asp Phe Tyr
        115                 120                 125

Cys Gln
    130

<210> SEQ ID NO 52
<211> LENGTH: 130
<212> TYPE: PRT
<213> ORGANISM: Bos sp.
```

-continued

```
<400> SEQUENCE: 52

Met Ala Trp Ser Leu Val Phe Leu Gly Val Val Leu Leu Ser Ala Phe
 1               5                  10                  15

Pro Gly Pro Ser Ala Gly Gly Arg Pro Met Pro Lys Leu Ala Asp Arg
                20                  25                  30

Lys Met Cys Ala Asp Glu Glu Cys Ser His Pro Ile Ser Val Ala Val
            35                  40                  45

Ala Leu Gln Asp Tyr Val Ala Pro Asp Cys Arg Phe Leu Thr Ile His
        50                  55                  60

Gln Gly Gln Val Val Tyr Ile Phe Ser Lys Leu Lys Gly Arg Gly Arg
 65                  70                  75                  80

Leu Phe Trp Gly Gly Ser Val Gln Gly Asp Tyr Tyr Gly Asp Gly Ala
                85                  90                  95

Ala Arg Leu Gly Tyr Phe Pro Ser Ser Ile Val Arg Glu Asp Gln Thr
            100                 105                 110

Leu Lys Pro Ala Lys Thr Asp Val Lys Thr Asp Ile Trp Asp Phe Tyr
        115                 120                 125

Cys Gln
    130

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Flag
      epitope sequence

<400> SEQUENCE: 53

Asp Tyr Lys Asp Asp Asp Asp Lys
 1               5
```

POLYPEPTIDE AND DNA THEREOF

FIELD OF THE INVENTION

The present invention relates to a novel secretory cell function regulating protein and its DNA.

BACKGROUND ART

Regardless of prokaryotic or eukaryotic, cells secret various proteins through mechanisms inherent to them. In particular, a multicellular organism (living body) exchanges intercellularly a variety of signals to maintain its differentiation, proliferation and homeostasis, and various humoral factors that play pivotal roles for the signal transduction are mostly secretory proteins or mature proteins. These factors are classified into hormones, neurotransmitters, cytokines, growth factors, etc., based on the structural and functional properties. Through the advanced recombinant DNA technology and cell culture technology in recent years, it has been steadily proceeded to clarify genes encoding these proteins and their protein structures. On the other hand, discovery of such factors have made a breakthrough in analysis of receptors of these factors expressed on the cell surface and further have led to clarification of mechanism on intracellular signal transduction, which will characterize the physiological function of the cells. In many diseases in human or under pathological conditions of model animal with various diseases, it is often found that abnormal expression of some humoral factor that should normally maintain homeostasis causes these diseases, which, as a result, will lead to exacerbation. In addition, there is a phenomenon applicable to diagnosis of various diseases, such as a so-called tumor marker, in which the accentuated expression specifically observed in cancer, and its expression-controlling mechanism is also an important target in pharmaceutical discovery research.

MIA (melanoma inhibitor activity) reported by Blesch et al. in 1994 is one of the secretory proteins falling within such a category. At first, MIA was isolated from the culture supernatant of melanoma cells using an anti-proliferating activity against human melanoma cells as is seen from its name, and its gene was also acquired (Cancer Research, 54, 5695–5701, 1994). Subsequently in 1996, a homologous gene to this protein was again identified by Sandell et al. as CD-RAP (bovine cartilage-derived retinoic acid-sensitive protein), suggesting that CD-RAP will function to form and maintain the formation and maintenance of joints from a physiological aspect (The Journal of Biological Chemistry, 271, 3311–3316, 1996). Though the MIA/CD-RAP gene has a homology as high as 85% or more between species of human mouse, rat and bovine, any known homologous protein has not been found so far. From genetic analysis in bovine and rat, it was also considered that there was no other gene similar to the MIA/CD-RAP gene (The Journal of Biological Chemistry, 271, 3311–3316, 1996).

On the other hand, structural analysis of the full-length DNA one organism possesses, i.e., genome, has already been decoded in bacteria, and human genome analysis will also be completed in a few years. The predicted number of genes is said to reach 100,000 in human. Indeed, many genes encoding the secretory proteins or secretory peptides have been isolated so far, but on the whole, it cannot be said that even these many genes cover all of the entire genome. In understanding the phenomena of life on an individual level, intercellular signal transduction that would occur there must be all explainable. It is highly likely that some unknown humoral functional molecules other than such known genes may play physiologically critical roles, and it has been strongly desired to find such substances.

The present invention aims at providing a novel cell function regulating secretory protein (hereinafter sometimes referred to as MLP protein or MLP), its partial peptide or salts thereof, a DNA encoding the protein, a recombinant vector, a transformant, a method for manufacturing the protein, a pharmaceutical composition comprising the protein or the DNA, an antibody to the protein, a method and kit for screening a receptor agonist/antagonist, a receptor agonist/antagonist obtainable by the screening, as well as a pharmaceutical comprising the receptor agonist/antagonist, and the like.

Isolation of a novel cell function regulating secretory protein can not only lead to a new finding on the mechanism of differentiation, proliferation, malignant alteration, etc., but also can make a further progress to clarify the phenomena of life, including ontogenesis, maintenance of homeostasis, etc. and exhibit an inhibitory activity against or a promoting activity for the protein, resulting in development of a novel pharmaceutical useful for the prevention, diagnosis and treatment of various diseases.

DISCLOSURE OF THE INVENTION

The present inventors have made extensive studies and as a result, succeeded in cloning cDNAs each having a novel base sequence, from human fetal brain- and mouse fetal brain-derived cDNA libraries. The present inventors have found that proteins encoded by the thus obtained cDNAs are precursor proteins of MIA/CD-RAP-like protein MLP having a useful cell function regulating secretory activity and MLP formed after cleaving signal sequence out of the MLP precursor is a secretory protein. Based on these findings, the present invention have made further investigations and come to accomplish the present invention.

That is, the present invention provides the following features.

(1) A polypeptide containing an amino acid sequence, which is the same or substantially the same as the amino acid sequence represented by SEQ ID NO:24, its amide or ester, or a salt thereof.

(2) The polypeptide, its amide or ester, or a salt thereof, according to (1), which comprises an amino acid sequence that is the same or substantially the same as the amino acid sequence represented by SEQ ID NO:6.

(3) The polypeptide or its amide or ester, or a salt thereof, according to (1), wherein substantially the same amino acid sequence represented by SEQ ID NO:24 is the amino acid sequence represented by SEQ ID NO:26.

(4) The polypeptide or its amide or ester, or a salt thereof, according to (2), wherein substantially the same amino acid sequence represented by SEQ ID NO:6 is the amino acid sequence represented by SEQ ID NO:12.

(5) The polypeptide or its amide or ester, or a salt thereof, according to (1), wherein substantially the same amino acid sequence represented by SEQ ID NO:24 is the amino acid sequence represented by SEQ ID NO:49.

(6) The polypeptide or its amide or ester, or a salt thereof, according to (2), wherein substantially the same amino acid sequence represented by SEQ ID NO:6 is the amino acid sequence represented by SEQ ID NO:47.

(7) A DNA containing a DNA bearing a base sequence encoding the polypeptide according to (1).

(8) The DNA according to (6), wherein the base sequence encoding the polypeptide according to (1) is the base sequence represented by SEQ ID NO:23.

(9) The DNA according to (6), wherein the base sequence encoding the polypeptide according to (1) is the base sequence represented by SEQ ID NO:4.

(10) The DNA according to (6), wherein the base sequence encoding the polypeptide according to (1) is the base sequence represented by SEQ ID NO:25.

(11) The DNA according to (6), wherein the base sequence encoding the polypeptide according to (1) is the base sequence represented by SEQ ID NO:10.

(12) The DNA according to (6), wherein the base sequence encoding the polypeptide according to (1) is the base sequence represented by SEQ ID NO:48.

(13) The DNA according to (6), wherein the base sequence encoding the polypeptide according to (1) is the base sequence represented by SEQ ID NO:46.

(14) A recombinant vector comprising the DNA according to (6).

(15) A transformant transformed with the recombinant vector according to claim 14.

(16) A method for manufacturing the polypeptide or its amide or ester, or a salt thereof, according to (1), which comprises culturing said transformant according to (15) and producing the polypeptide according to (1).

(17) An antibody to the polypeptide or its amide or ester, or a salt thereof, according to (1).

(18) A method of screening a compound or its salt that promotes or inhibits the activity of the polypeptide or its salt according to (1), which comprises using the polypeptide, its amide or ester, or a salt thereof, according to (1).

(19) A kit for screening a compound or its salt that promotes or inhibits the activity of the polypeptide, its amide or ester, or a salt thereof, according to (1), comprising the polypeptide or its salt according to (1).

(20) A compound or its salt that promotes or inhibits the activity of the polypeptide, its amide or ester, or a salt thereof, according to (1), which is obtainable using the screening method according to (18) or using the screening kit according to (19).

(21) A pharmaceutical comprising a compound or its salt that promotes or inhibits the activity of the polypeptide, its amide or ester, or a salt thereof, according to (1), which is obtainable using the screening method according to (18) or using the screening kit according to (19).

(22) A pharmaceutical comprising the polypeptide, its amide or ester, or a salt thereof, according to (1).

(23) An agent for the prevention/treatment of bone and joint diseases or pathologic angiogenesis, comprising the polypeptide, its amide or ester, or a salt thereof, according to (1).

(24) A diagnostic agent comprising the antibody according to (17).

The present invention further relates to the following features.

(25) The polypeptide, its amide or ester, or a salt thereof, according to (1), wherein substantially the same amino acid sequence as that represented by SEQ ID NO:24 is an amino acid sequence having homology of at least about 50% (preferably at least about 60%, more preferably at least about 70%, much more preferably at least about 80%, further much more preferably at least about 90%, and most preferably about 95%), to the amino acid sequence represented by SEQ ID NO:24.

(26) The polypeptide, its amide or ester, or a salt thereof, according to (1), wherein substantially the same amino acid sequence as the amino acid sequence shown by SEQ ID NO:24 is (i) an amino acid sequence represented by SEQ ID NO:24, of which 1 or 2 more (preferably approximately 1 to 30) amino acids are deleted; (ii) an amino acid sequence represented by SEQ ID NO:24, to which 1 or 2 more (preferably approximately 1 to 40, more preferably approximately 1 to 30) amino acids are added; (iii) an amino acid sequence represented by SEQ ID NO:24, in which 1 or 2 more (preferably approximately 1 to 30) amino acids are substituted by other amino acids; and (iv) a combination of the above amino acid sequences.

Furthermore, the DNA, polypeptide or its amide or ester or a salt thereof, etc. of the present invention can be utilized for basic studies, including molecular weight markers, tissue markers, chromosomal mapping, identification of hereditary diseases, design or primers or probes, etc.

BRIEF DESCRIPTION OF THE DRAWINGS

FIG. 1 shows the amino acid sequences of human MLP precursor (hMLP)(SEQ ID NO: 6), mouse MLP precursor (mMLP)(SEQ ID NO: 12), human MIA precursor (hMIA) (SEQ ID NO: 3), mouse MIA precursor (mMIA)(SEQ ID NO: 9), rat MIA precursor (rMIA)SEQ ID NO: 51) and bovine MIA precursor (bMIA)(SEQ ID NO: 52).

In the figure, Lanes 1, 2, 3, 4, 5 and 6 designate lanes obtained by electrophoresis of the culture supernatants of COS-7 cells introduced with mouse MLP (no FLAG tag), mouse MLP-FLAG, mouse MIA (no FLAG tag), mouse MIA-FLAG, human MLP (no FLAG tag) and mouse MLP-FLAG, respectively.

Figure 3:
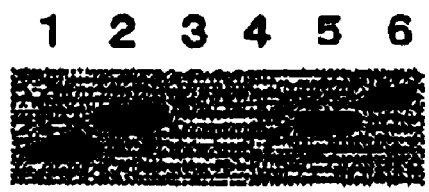

FIG. 3 shows the results of Western blotting analysis performed in EXAMPLE 6, in which anti-MLP antibody was employed as a primary antibody.

In the figure, Lanes 1, 2, 3, 4, 5 and 6 designate lanes obtained by electrophoresis of the culture supernatants of COS-7 cells introduced with mouse MLP (no FLAG tag), mouse MLP-FLAG, mouse MIA (no FLAG tag), mouse MIA-FLAG, human MLP (no FLAG tag) and mouse MLP-FLAG, respectively.

Figure 4:
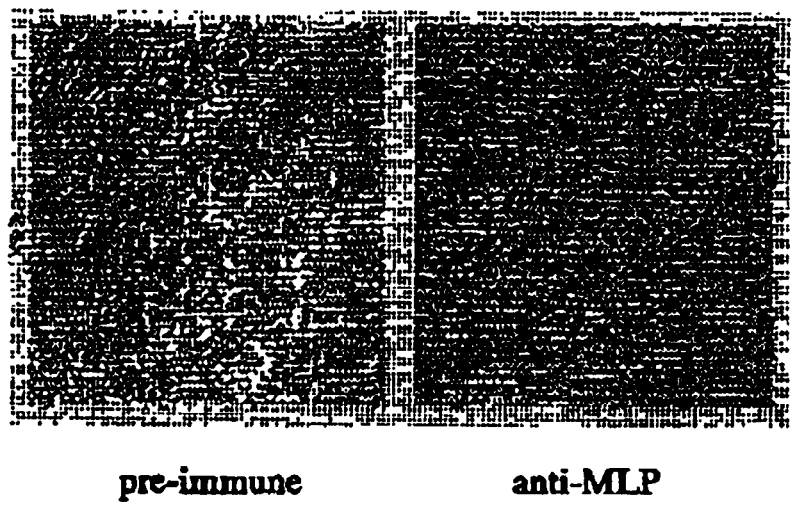

FIG. 4 shows the results of immunostaining performed in EXAMPLE 6, in which the left panel indicates the result of control experiment using pre-immune rabbit sera and the right panel indicates the results obtained using anti-MLP antisera.

BEST MODE OF EMBODIMENT OF THE INVENTION

The polypeptide of the present invention containing the amino acid sequence represented by SEQ ID NO:24 (hereinafter sometimes referred to as human type polypeptide), the polypeptide containing the amino acid sequence represented by SEQ ID NO:26 (hereinafter sometimes referred to as mouse type polypeptide), the polypeptide containing the amino acid sequence represented by SEQ ID NO:49 (hereinafter sometimes referred to as rat type polypeptide) and the polypeptide containing an amino acid sequence, which is substantially the same as the human type polypeptide (hereinafter the human type polypeptide and the polypeptide containing an amino acid sequence, which is substantially the same as the human type polypeptide are sometimes collectively referred to as the polypeptide of the present invention) may be any polypeptide derived from any cells of human and other warm-blooded animals (e.g., guinea pig, rat, mouse, chicken, rabbit, swine, sheep, bovine, monkey, etc.) (e.g., liver cells, splenocytes, nerve cells, glial cells, □ cells of pancreas, bone marrow cells, mesangial cells, Langerhans cells, epidermic cells, epithelial cells, endothelial cells, fibroblasts, fibrocytes, myocytes, fat cells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, or interstitial cells; the corresponding precursor cells, stem cells, cancer cells, etc.); or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone and joint, skeletal muscle, etc.; the poly peptides may also be recombinant polypeptides or synthetic polypeptides.

When the polypeptide of the present invention carries a signal peptide, the polypeptide can be extracellularly secreted efficiently.

The amino acid sequence which is substantially the same as the amino acid sequence represented by SEQ ID NO:24 includes an amino acid sequence having homology of at least about 50%, preferably at least about 60%, more preferably at least about 70%, much more preferably at least about 80%, further much more preferably at least about 90%, and most preferably about 95%, to the amino acid sequence represented by SEQ ID NO:24, and specific examples of such amino acid sequences are the amino acid sequence represented by SEQ ID NO:26, the amino acid sequence represented by SEQ ID NO:49, and the like.

The polypeptide containing the amino acid sequence represented by SEQ ID NO:24 is sometimes referred to as human MLP or human MLP protein; the amino acid sequence represented by SEQ ID NO:26 is sometimes referred to as mouse MLP or mouse MLP protein; the amino acid sequence represented by SEQ ID NO:49 is sometimes referred to as rat MLP or rat MLP protein; and these polypeptides are sometimes collectively referred to as MLP.

Specific examples of the polypeptide containing the amino acid sequence shown by SEQ ID NO:24 or an amino acid sequence which is substantially the same as the amino acid sequence shown by SEQ ID NO:24 include the polypeptide containing the amino acid sequence shown by SEQ ID NO:6 or an amino acid sequence which is substantially the same as the amino acid sequence shown by SEQ ID NO:6, and the like.

The amino acid sequence which is substantially the same as the amino acid sequence represented by SEQ ID NO:6 includes an amino acid sequence having homology of at least about 50%, preferably at least about 60%, more preferably at least about 70%, much more preferably at least about 80%, further much more preferably at least about 90%, and most preferably about 95%, to the amino acid sequence represented by SEQ ID NO:6, and specific examples of such amino acid sequences are the amino acid sequence represented by SEQ ID NO:12, the amino acid sequence represented by SEQ ID NO:47, and the like.

The polypptide containing the amino acid sequence represented by SEQ ID NO:6 is sometimes referred to as human MLP precursor or human MLP precursor protein; the amino acid sequence represented by SEQ ID NO:12 is sometimes referred to as mouse MLP precursor or mouse MLP precursor protein; the amino acid sequence represented by SEQ ID NO:47 is sometimes referred to as rat MLP precursor or rat MLP precursor protein; and they are sometimes collectively referred to as MLP precursors.

Preferred examples of the polypeptide of the present invention containing an amino acid sequence, which is substantially the same as the amino acid sequence shown by SEQ ID NO:24, include a polypeptide containing an amino acid sequence, which is substantially the same as the amino acid sequence shown by SEQ ID NO:24 and has a property substantially equivalent to that of the polypeptide having the amino acid sequence shown by SEQ ID NO:24, and the like.

Preferred examples of the polypeptide containing an amino acid sequence which is substantially the same amino acid sequence represented by SEQ ID NO:6, include a polypeptide containing an amino acid sequence, which is substantially the same as the amino acid sequence shown by SEQ ID NO:6 and has a property substantially equivalent to that of the polypeptide having the amino acid sequence shown by SEQ ID NO:6, and the like.

The substantially equivalent property includes, for example, an activity that is secreted and acts as a humoral factor, and the like. The term substantially equivalent is used to mean that these activities are equivalent qualitatively. Therefore, it is preferred that activities such as a secretory activity, solubility, etc. are equivalent (e.g., about 0.1 to about 100 times, preferably about 0.5 to about 10 times, more preferably about 0.5 to about 2 times), but it is allowable that differences in quantitative factor such as strength of these activities, molecular weight of the polypeptide may be present.

More specifically, the polypeptide containing an amino acid sequence, which is substantially the same amino acid sequence represented by SEQ ID NO:24 or SEQ ID NO:6, includes a so-called mutein such as a polypeptide containing (i) an amino acid sequence represented by SEQ ID NO:24 or SEQ ID NO:6, of which 1 or 2 more (preferably approximately 1 to 30, more preferably approximately 1 to 10 and most preferably several (1 to 5) amino acids have been deleted; (ii) an amino acid sequence represented by SEQ ID NO:24 or SEQ ID NO:6, to which 1 or 2 more (preferably approximately 1 to 40, more preferably approximately 1 to 30, much more preferably approximately 1 to 10 and most preferably several (1 to 5) amino acids have been added; (iii) an amino acid sequence represented by SEQ ID NO:24 or SEQ ID NO:6, into which 1 or 2 more (preferably approximately 1 to 30, more preferably approximately 1 to 10 and most preferably several (1 to 5) amino acids have been inserted, (iv) an amino acid sequence represented by SEQ ID NO:24 or SEQ ID NO:6, in which 1 or 2 more (preferably approximately 1 to 30, more preferably approximately 1 to 10 and most preferably several (1 to 5) amino acids have been substituted by other amino acids; and (v) a combination of the above amino acid sequences, and the like.

When an amino-acid sequence(s) have been inserted, deleted or substituted as described above, the positions of such insertion, deletion or substitution are not particularly limited, but examples of the positions are the position other than that for the amino acid sequence common to the amino acid sequences shown by SEQ ID NO:24, SEQ ID NO:26 and SEQ ID NO:49, the position other than that for the amino acid sequence common to the amino acid sequences shown by SEQ ID NO:6, SEQ ID NO:12 and SEQ ID NO:47, etc.

Throughout the present specification, the polypeptides are represented in accordance with the conventional way of describing polypeptides, that is, the N-terminus (amino terminus) at the left hand and the C-terminus (carboxyl terminus) at the right hand. In the polypeptides of the present invention including the polypeptide containing the amino acid sequence shown by SEQ ID NO:24, the C-terminus is usually in the form of a carboxyl group (—COOH) or a carboxylate (—COO—) but may be in the form of an amide (—CONH$_2$) or an ester (—COOR).

Herein, examples of the ester group shown by R include a C$_{1-6}$ alkyl group such as methyl, ethyl, n-propyl, isopropyl, n-butyl, etc.; a C$_{3-8}$ cycloalkyl group such as cyclopentyl, cyclohexyl, etc.; a C$_{6-12}$ aryl group such as phenyl, □-naphthyl, etc.; a C$_{7-14}$ aralkyl such as a phenyl-C$_{1-2}$ alkyl group, e.g., benzyl, phenethyl, etc.; an □-naphthyl-C$_{1-2}$ alkyl group such as □-naphthylmethyl, etc.; and the like. In addition, pivaloyloxymethyl or the like which is used widely as an ester for oral administration may also be used.

Where the polypeptide of the present invention contains a carboxyl group (or a carboxylate) at a position other than the C-terminus, it may be amidated or esterified and such an amide or ester is also included within the polypeptide of the present invention. The ester group may be the same group as that described with respect to the above C-terminal.

Furthermore, examples of the polypeptide of the present invention include variants of the above polypeptides, wherein the amino group at the N-terminus (e.g., methionine residue) of the polypeptide is protected with a protecting group (e.g., a C$_{1-6}$ acyl group such as a C$_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a C$_{1-6}$ acyl group such as a C$_{1-6}$ alkanoyl group, e.g., formyl group, acetyl group, etc.), or conjugated proteins such as glycoproteins having sugar chains.

The polypeptide of the present invention or salts thereof may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The polypeptide of the present invention or salts thereof may be manufactured by a publicly known method used to purify a polypeptide (protein) from human or other warm-blooded animal cells or tissues described above, or may also be manufactured by culturing a transformant containing DNA encoding the polypeptide later described. Furthermore, the polypeptide of the present invention or salts thereof may also be manufactured by a modification of the peptide synthesis method, which will be described hereinafter.

Where the polypeptide or salts thereof are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the polypeptide of the present invention, its salts or amides, commercially available resins that are used for polypeptide (protein) synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2';4'-dimethoxyphenylhydroxymethyl)phenoxy resin, 4-(2',4'-dimethoxyphenyl-Fmoc-aminoethyl)phenoxy resin, etc. Using these resins, amino acids in which α-amino groups and functional groups on the side chains are appropriately protected are condensed on the resin in the order of the sequence of the objective polypeptide according to various condensation methods publicly known in the art. At the end of the reaction, the polypeptide is excised from the resin and at the same time, the protecting groups are removed. Then, intramolecular disulfide bond-forming reaction is performed in a highly diluted solution to obtain the objective polypeptide or amides thereof.

For condensation of the protected amino acids described above, a variety of activation reagents for polypeptide synthesis may be used, but carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for polypeptide (protein) condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide (protein) binding reactions and is usually selected in the range of approximately −20° C. to 50° C. The activated amino acid derivatives are used generally in an excess of 1.5 to 4 times. The condensation is examined using the ninhydrin reaction; when the condensation is insufficient the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, tbutoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting materials include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the activated amino acids in which the amino-groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such: as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the polypeptide, for example, the a-carboxyl group of the carboxy terminal amino acid is first protected by amidation; the peptide (polypeptide) chain is then extended to the amino group side to a desired length. Thereafter, a polypeptide in which only the protecting group of the N-terminal α-amino group of the peptide chain has been eliminated from the polypeptide and a polypeptide in which only the protecting group of the C-terminal carboxyl group has been eliminated are manufactured. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired polypeptide.

To prepare the esterified polypeptide of the present invention, for example, the α-carboxyl group of the carboxy terminal amino acid is condensed with a desired alcohol to prepare the amino acid ester, which is followed by procedure similar to the preparation of the amidated polypeptide above to give the desired esterified polypeptide or partial peptide.

The polypeptide of the present invention or its salts can be manufactured by publicly known methods for peptide synthesis. For the methods for peptide synthesis, for example, either solid phase synthesis or liquid phase synthesis may be used. That is, the partial peptide or amino acids that can constitute the objective peptide of the present invention are condensed with the remaining part of the partial peptide. Where the product contains protecting groups, these protecting groups are removed to give the desired peptide. Publicly known methods for condensation and elimination of the protecting groups are described in (1)–(5) below.

(1) M Bodanszk & M. A. Ondetti: Peptide Synthesis, Interscience Publishers, New York (1966)

(2) Schroeder & Luebke: The Peptide, Academic Press, New York (1965)

(3) Nobuo Izumiya, et al.: *Peptide Gosei-no-Kiso to Jikken* (Basics and experiments of peptide synthesis), published by Maruzen Co. (1975)

(4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

(5) Haruaki Yajima ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the polypeptide of the present invention. When the polypeptide obtained by the above methods is in a free form, the polypeptide can be converted into an appropriate salt by a publicly known method; when the polypeptide is obtained in a salt form, it can be converted into a free form or a different salt form by a publicly known method.

The DNA encoding the polypeptide of the present invention may be any DNA so long as it comprises the base sequence encoding the polypeptide of the present invention described above. Such a DNA may also be any one of genomic DNA, cDNA derived from the cells or tissues described above and synthetic DNA.

The vector to be used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

Specifically, the DNA encoding the polypeptide of the present invention may be any one of, for example, DNA comprising the base sequence represented by SEQ ID NO:23, or any DNA having a base sequence hybridizable to the base sequence represented by SEQ ID NO:23under high stringent conditions and encoding a polypeptide which has the activities substantially equivalent to those of the polypeptide of the present invention (e.g., immunogenicity, etc.).

As the DNA comprising the base sequence represented by SEQ ID NO:23, there is employed a DNA comprising the base sequence represented by SEQ ID NO:24, or the like.

Specific examples of the DNA that is hybridizable to the base sequence represented by SEQ ID NO:23 under high stringent conditions include DNA comprising at least about 60% homology, preferably at least about 70% homology, and most preferably at least about 80% homology, to the base sequence represented by SEQ ID NO:23, and the like.

Also, specific examples of the DNA encoding the polypeptide of the present invention include DNA comprising the base sequence represented by SEQ ID NO:25, DNA having a base sequence, which is hybridizable to the base sequence represented by SEQ ID NO:25 under high stringent conditions, encodes a polypeptide which has the activities substantially equivalent to those of the polypeptide of the present invention (e.g., immunogenicity, etc.) and has a property substantially equivalent to that of the polypeptide of the present invention.

As the DNA that is hybridizable to the base sequence represented by SEQ ID NO:25 under high stringent conditions, there is employed DNA comprising at least about 60% homology, preferably at least about 70% homology, and most preferably at least about 80% homology, to the base sequence represented by SEQ ID NO:25, and the like. Specifically, DNA comprising the base sequence represented by SEQ ID NO:10, or the like is employed.

Also, specific examples of the DNA hybridizable to the base sequence represented by SEQ ID NO:23 under high stringent conditions, include DNA comprising a base sequence shown by SEQ ID NO:48, or DNA encoding a polypeptide, which comprises a base sequence hybridizable to the base sequence represented by SEQ ID NO:48 under high stringent conditions, bears DNA or the like encoding a polypeptide which has the activities substantially equivalent to those of the polypeptide of the present invention (e.g., immunogenicity, etc.) and has a property substantially equivalent to that of the polypeptide of the present invention, and the like.

As the DNA that is hybridizable to the base sequence represented by SEQ ID NO:48 under high stringent conditions, there is employed DNA having at least about 60% homology, preferably at least about 70% homology, and most preferably at least about 80% homology, to the base sequence represented by SEQ ID NO:48, and the like. Specifically, DNA containing the base sequence represented by SEQ ID NO:41 or SEQ ID NO:46, or the like is employed.

The hybridization can be carried out by publicly known methods or by a modification thereof, for example, according to the method described in Molecular Cloning, 2nd. (J. Sambrook et al., Cold Spring Harbor Lab. Press, 1989). A commercially available library may also be used according to the instructions of the attached manufacturer's protocol. The hybridization can be carried out preferably under high stringent conditions.

The high stringent conditions are, for example, those in a sodium concentration at about 19 mM to about 40 mM, preferably about 19 mM to about 20 mM at a temperature of about 50° C. to about 70° C., preferably about 60° C. to about 65° C.

For the DNA encoding the polypeptide of the present invention containing the amino acid sequence represented by SEQ ID NO:24, there may be employed DNA having the base sequence represented by SEQ ID NO:23, etc. and, DNA having the base sequence represented by SEQ ID NO:4 may be used for the DNA encoding the polypeptide of the present invention having the amino acid sequence represented by SEQ ID NO:6. For the DNA encoding the polypeptide having the amino acid sequence represented by SEQ ID NO:26, DNA having the base sequence represented by SEQ ID NO:25 may be employed and, DNA having the base sequence represented by SEQ ID NO:10 may be used as the DNA encoding the polypeptide having the amino acid sequence represented by SEQ ID NO:12. As the DNA encoding the polypeptide having the amino acid sequence represented by SEQ ID NO:49, there may be employed DNA having the base sequence represented by SEQ ID NO:48 and, DNA having the base sequence represented by SEQ ID NO:46 may be used for the DNA encoding the polypeptide having the amino acid sequence represented by SEQ ID NO:47.

For cloning of the DNA that entirely encodes the polypeptide of the present invention, the DNA may be either amplified by publicly known PCR using synthetic DNA primers containing a part of the base sequence of the polypeptide of the present invention, or the DNA inserted into an appropriate vector can be selected by hybridization with a labeled DNA fragment or synthetic DNA that encodes a part or entire region of the polypeptide of the present invention. The hybridization can be carried out, for example, according to the method described in Molecular Cloning, 2nd (J. Sambrook et al., Cold Spring Harbor Lab. Press, 1989). The hybridization may also be performed using commercially available library in accordance with the protocol described in the attached instructions.

Substitution of the base sequence of DNA can be effected by PCR or publicly known methods such as the Gapped duplex method or the Kunkel method, or its modification using a publicly known kit available as Mutan™ G or Mutan™ K (both manufactured by Takara Shuzo Co., Ltd., trademark).

The cloned DNA encoding the polypeptide can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the polypeptide of the present invention can be manufactured, for example, by (a) excising the desired DNA fragment from the DNA encoding the polypeptide of the present invention, (b) and then ligating the DNA fragment with an appropriate expression vector downstream a promoter in the vector.

Examples of the vector include plasmids derived form *E. coli* (e.g., pBR322, pBR325, pUC12, pUC13), plasmids derived from Bacillus subtilis (e.g., pUB110, pTP5, pC194), plasmids derived from yeast (e.g., pSH19, pSH15), bacteriophages such as ☐ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SR□ promoter, SV40 promoter, LTR promoter, CMV promoter, HSV-TK promoter, β-actin, etc.

Among them, CMV (cytomegalovirus) promoter, SRα promoter or the like is preferably used. Where the host is bacteria of the genus Escherichia, preferred examples of the promoter include trp promoter, lac promoter, recA promoter, □PL promoter, lpp promoter, T17 promoter, etc. In the case of using bacteria of the genus Bacillus as the host, preferred example of the promoter are SPO1 promoter, SP02 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40 ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, Geneticin resistance), etc. In particular, when dhfr gene is used as the selection marker together with dhfr gene deficient Chinese hamster cells, recombinant somatic cells can also be selected on thymidine free media.

If necessary and desired, a signal sequence that matches with a host is added to the N-terminus of the polypeptide of the present invention. Examples of the signal sequence that can be used are Pho A signal sequence, OmpA signal sequence, etc. in the case of using bacteria of the genus Escherichia as the host; □-amylase signal sequence, subtilisin signal sequence, etc. in the case of using bacteria of the genus Bacillus as the host; MFα signal sequence, SUC2 signal sequence, etc. in the case of using yeast as the host; and insulin signal sequence, □-interferon signal sequence, antibody molecule signal sequence, etc. in the case of using animal cells as the host, respectively.

Using the vector comprising the DNA encoding the polypeptide of the present invention thus constructed, transformants can be manufactured.

Examples of the host, which may be employed, are bacteria belonging to the genus Escherichia, bacteria belonging to the genus Bacillus, yeast, insect cells, insects and animal cells, etc.

Specific examples of the bacteria belonging to the genus Escherichia include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of the bacteria belonging to the genus Bacillus include *Bacillus subtilis* M1114 (Gene, 24;255 (1983)), 207–21 (Journal of Biochemistry, 95, 87 (1984)), etc.

Examples of yeast include *Saccharomyces cerevisiae* AH22, AH22R, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc.; and for the virus BmNPV, *Bombyx mori* N cells (BmN cells), etc. is used. Examples of the Sf cells which can be used are Sf9 cells (ATCC CRL1711) and Sf21 cells (both cells are described in Vaughn, J. L. et al., In Vivo, 13, 213–217 (1977).

As the insect, for example, a larva of *Bombyx mori* can be used (Maeda et al., Nature, 315, 592 (1985)).

Examples of animal cells include monkey cell COS-7, Vero, Chinese hamster cells CHO (hereinafter referred to as CHO cells), dhfr gene deficient Chinese hamster cells CHO (hereinafter simply referred to as CHO(dhfr) cells), mouse L cells, mouse AtT-20, mouse myeloma cells, rat GH 3, human FL cells, etc.

Bacteria belonging to the genus Escherichia can be transformed, for example, by the method described in Proc. Natl. Acad. Sci. U.S.A., 69, 2110 (1972) or Gene, 17,107 (1982).

Bacteria belonging to the genus Bacillus can be transformed, for example, by the method described in Molecular & General Genetics, 168, 111 (1979).

Yeast can be transformed, for example, by the method described in Methods in Enzymology, 194, 182–187 (1991) or Proc. Natl. Acad. Sci. U.S.A., 75, 1929 (1978).

Insect cells or insects can be transformed, for example, according to the method described in Bio/Technology, 6, 47–55(1988).

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263–267 (1995), published by Shujunsha, or Virology, 52, 456 (1973).

Thus, the transformant transformed with the expression vector comprising the DNA encoding the polypeptide can be obtained.

Where the host is bacteria belonging to the genus Escherichia or the genus Bacillus, the transformant can be appropriately incubated in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, yeast extract, meat extract, soybean cake, potato extract, etc. Examples of the inorganic materials are calcium chloride, sodium dihydrogenphosphate, magnesium chloride, etc. In addition, yeast extract, vitamins, growth promoting factors, etc. may also be added to the medium. Preferably, pH of the medium is adjusted to about 5 to about 8.

A preferred example of the medium for incubation of the bacteria belonging to the genus Escherichia is M9 medium supplemented with glucose and Casamino acids (Miller, Journal of Experiments in Molecular Genetics, 431–433, Cold Spring Harbor Laboratory, New York, 1972). If necessary and desired, a chemical such as 3□-indolylacrylic acid can be added to the medium thereby to function the promoter efficiently.

Where the bacteria belonging to the genus Escherichia are used as the host, the transformant is usually cultivated at about 15° C. to about 43° C. for about 3 hours to about 24 hours. If necessary and desired, the culture may be aerated or agitated.

Where the bacteria belonging to the genus Bacillus are used as the host, the transformant is cultivated generally at about 30° C. to about 40° C. for about 6 hours to about 24 hours. If necessary and desired, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to about 35° C. for, about 24 hours to about 72 hours. If necessary and desired, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal calf serum [Science, 122, 501 (1952)], DMEM medium [Virology, 8, 396 (1959)], RPMI 1640 medium [The Journal of the American Medical Association, 199, 519 (1967)]1199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, the polypeptide of the present invention can be produced intracellularly or extracellularly in the transformant.

The polypeptide of the present invention can be separated and purified from the culture described above by the following procedures.

When the polypeptide of the present invention is extracted from the culture or cells, after cultivation the cell or transformant is collected by a publicly known method and suspended in a appropriate buffer. The cell or transformant is then disrupted by publicly known methods such as ultrasonication, a treatment with lysozyme and/or freeze-thaw, etc. followed by centrifugation or filtration. Thus, the crude extract of the polypeptide can be obtained. The buffer used for the procedures may contain a protein modifier such as urea or guanidine hydrochloride, or a surfactant such as Triton X-100™, etc. When the polypeptide is secreted in the culture broth, after completion of the cultivation the supernatant can be separated from the cell or transformant to collect the supernatant by a publicly known method.

The supernatant or the polypeptide contained in the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the polypeptide thus obtained is in a free form, it can be converted into the salt by publicly known methods or modifications thereof. On the other hand, when the polypeptide is obtained in the form of a salt, it can be converted into the free form or in the form of a different salt by publicly known methods or modifications thereof.

The polypeptide produced by the recombinant can be treated, prior to or after the purification, with an appropriate protein modifying enzyme so that the polypeptide can be appropriately modified to remove a part of the polypeptide. Examples of these enzymes include trypsin, chymotrypsin, arginyl endopeptidase, protein kinase, glycosidase and the like.

The activity of the thus produced polypeptide of the present invention or salts thereof can be determined by an enzyme immunoassay using a specific antibody, Western blot analysis, etc.

Antibodies to the polypeptide of the present invention or salts thereof may be any of polyclonal antibodies and monoclonal antibodies, as long as they are capable of recognizing the polypeptide of the present invention or salts thereof.

The antibodies to the polypeptide of the present invention or salts thereof may be manufactured by publicly known methods for manufacturing antibodies or antisera, using as antigens the polypeptide of the present invention.

Preparation of Monoclonal Antibody (a) Preparation of Monoclonal Antibody-producing Cells The polypeptide of the present invention or its salt is administered to warm-blooded animals either solely or together with carriers or diluents to the site, in which the production of antibody is possible by the administration. In order to potentiate the antibody productivity upon the administration, complete Freund's adjuvants or incomplete Freund's adjuvants may be administered. The administration is usually carried out once every two to six weeks and approximately two to ten times in total. Examples of the applicable warm-blooded animals are monkeys, rabbits, dogs, guinea pigs, mice, rats, sheep, goats, chickens and the like, with the use of mice and rats being preferred.

In the preparation of monoclonal antibody-producing cells, a warm-blooded animal, e.g., mice, immunized with an antigen wherein the antibody titer is recognized is selected, then spleen or lymph node is collected after two to five days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled form of the polypeptide, which will be described later, with the antiserum followed by assaying the binding activity of the labeling agent bound to the antibody. The fusion may be carried out, for example, using the known method by Koehler and Milstein [Nature, 256, 495, (1975)]. Examples of the fusion accelerator are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubating at 20 to 40° C., preferably at 30 to 37° C. for about 1 to about 10 minutes, an efficient cell fusion can be carried out.

Various methods can be used for screening of monoclonal antibody-producing hybridomas. Examples of such methods include a method which comprises adding the supernatant of hybridoma to a solid phase (e.g., microplate) adsorbed with, e.g., a polypeptide antigen directly or together with a carrier, adding an anti-immunoglobulin antibody (when mouse cells are used for the cell fusion, anti-mouse immunoglobulin antibody is used) labeled with a radioactive substance or an enzyme, or adding Protein A and detecting the monoclonal antibody bound to the solid phase, and a method which comprises adding the supernatant of hybridoma to a solid phase adsorbed with an anti-immunoglobulin antibody or Protein A, adding the polypeptide labeled with a radioactive substance or an enzyme and detecting the monoclonal antibody bound to the solid phase.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium containing about 1% to about 20%, preferably about 10% to about 20% fetal calf serum, GIT medium (Wako Pure Chemical Industries, Ltd.) containing 1% to 10% fetal calf serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody Separation and purification of a monoclonal antibody can be carried out by publicly known methods, such as separation and purification of immunoglobulins [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody).

Preparation of Polyclonal Antibody

The polyclonal antibody of the present invention can be manufactured by publicly known methods or modifications thereof. For example, a warm-blooded animal is immunized with an immunogen (polypeptide antigen) per se, or a complex of immunogen and a carrier protein is formed and a warm-blooded animal is immunized with the complex in a manner similar to the method described above for the manufacture of monoclonal antibodies. The product containing the antibody to the polypeptide of the present invention or its salt is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin, hemocyanin or the like is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester, activated ester reagents containing thiol group or dithiopyridyl group and the like are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every about 2 to about 6 weeks and about 3 to about 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The antisense DNA having a complementary or substantially complementary base sequence to the DNA encoding the polypeptide of the present invention can be any antisense DNA so long as it possesses a base sequence a complementary or substantially complementary base sequence to that of the DNA of the present invention and capable of suppressing expression of the DNA.

The base sequence substantially complementary to the DNA of the present invention may, for example, be a base sequence having at least about 70% homology, preferably at least about 80% homology, more preferably at least about 90% homology and most preferably at least about 95% homology, to the full-length base sequence or partial base sequence of the base sequence complementary to the DNA of the present invention (i.e., complementary strand to the DNA of the present invention). Particularly in the entire base sequence of the complementary strand to the DNA of the present invention, an antisense DNA having at least about 70% homology, preferably at least about 80% homology, more preferably at least about 90% homology and most preferably at least about 95% homology, to the complementary strand of the base sequence which encodes the N-terminal region of the polypeptide of the present invention (e.g., the base sequence around the initiation codon). These antisense DNAs can be synthesized using a publicly known DNA synthesizer, etc.

In the case that the polypeptide of the present invention has a signal peptide, it is efficiently secreted extracellularly to exhibit as a humoral factor important biological activities such as signal transduction, self defense, etc.

Hereinafter the uses of the polypeptide of the present invention or salts thereof (hereinafter sometimes merely referred to as the polypeptide of the present invention); DNA encoding the polypeptide of the present invention (hereinafter sometimes merely referred to as the DNA of the present invention), antibodies to the polypeptide of the present invention, or salts thereof (hereinafter sometimes merely referred to as the antibody of the present invention) and the antisense DNA.

(1) Since the polypeptide of the present invention is expressed specifically to cartilage tissues, the polypeptide can be used as a tissue marker. That is, the polypeptide is useful as a marker for detecting the differentiation, pathological conditions, metastasis of cancer, etc. The polypeptide is also applicable to fractionation of the corresponding receptors, ligands, bound polypeptides, etc. Furthermore, the polypeptide may be formed into a panel for publicly known high through-put screening, which can be utilized for exploring biological activities. In addition, through the chromosomal mapping, the polypeptide is also available for studies on genetic diseases.

(2) Therapeutic/prophylactic agent for the diseases with which the polypeptide of the present invention of the present invention is associated Since the polypeptide of the present invention is present in vivo (especially in the cartilage tissue) as a humoral factor and has a function to suppress differentiation of cartilage, any abnormality or deficiency of the polypeptide of the present invention or the DNA of the present invention or any abnormal reduction or accentuation in the expression amount of the polypeptide or the DNA would cause a variety of diseases.

When the DNA, etc. of the present invention is deficient or its expression amount is abnormally reduced, such would cause various diseases including bone and joint diseases, e.g., arthritis deformans, chronic articular rheumatism, marble stone disease, etc.; or pathological angiogenesis, etc.

Therefore, the polypeptide of the present invention and the DNA of the present invention can be used as pharmaceuticals such as agents for the treatment/prevention of various diseases such as bone and joint diseases, e.g., arthritis deformans, chronic articular rheumatism, marble stone disease, etc.; or pathological angiogenesis, etc.

When a patient has a reduced level of, or deficient of the polypeptide of the present invention in his or her body so that signal transduction in cells does not work sufficiently or normally, the DNA of the present invention can provide its role sufficiently or properly for the patient, (a) by administering the DNA of the present invention to the patient to express the polypeptide of the present invention in vivo (b) by inserting the DNA of the present invention into a cell, expressing the polypeptide of the present invention and then transplanting the cell to the patient, or (c) by administering the polypeptide of the present invention to the patient.

Where the DNA of the present invention is used as the prophylactic/therapeutic agents described above, the DNA per se can be administered directly to human or other warm-blooded animal; alternatively, the DNA can be inserted into an appropriate vector such as retrovirus vector, adenovirus vector, adenovirus-associated virus vector, etc. and then administered to human or other warm-blooded animal in a conventional manner. The DNA of the present invention may also be administered as naked DNA, or with adjuvants to assist its uptake by gene gun or through a catheter such as a catheter with a hydrogel.

Where the polypeptide of the present invention is used as the aforesaid therapeutic/prophylactic agents, the polypeptide is advantageously used on a purified level of at least 90%, preferably at least 95%, more preferably at least 98% and most preferably at least 99%.

The polypeptide of the present invention can be used orally, for example, in the form of tablets which may be sugar coated if necessary and desired, capsules, elixirs, microcapsules etc., or parenterally in the form of injectable preparations as a sterile solution and a suspension in water or with other pharmaceutically acceptable liquid. These preparations can be manufactured by mixing the polypeptide of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™, HCO-50, etc.) and the like. Examples of the oily medium include sesame oil and soybean oil, which may also be used in combination with a dissolution aid such as benzyl benzoate and benzyl alcohol. The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector in which the DNA of the present invention is inserted may also be prepared into pharmaceutical preparations in a manner similar to the procedures above. Such preparations are generally used parenterally.

Since the thus obtained pharmaceutical preparation is safe and low toxic, the preparation can be administered to human or other warm-blooded animal (e.g., rat, mouse, guinea pig, rabbit, chicken, sheep, swine, bovine, horse, cat, dog, monkey, etc.).

The dose of the polypeptide of the present invention varies depending on target disease, subject to be administered, route for administration, etc.; for example, in oral administration for the treatment of bone and joint disease, the polypeptide of the present invention is normally administered in a dose of about 1 mg to about 1000 mg, preferably about 10 to about 500 mg, and more preferably about 10 to about 200 mg per day for adult (as 60 kg body weight). In parenteral administration, the single dose of the polypeptide of the present invention varies depending on subject to be administered, target disease, etc. but it is advantageous for the treatment of bone and joint disease to administer the active ingredient intravenously at a daily dose of about 1 to about 1000 mg, preferably about 1 to about 200 mg, and more preferably about 10 to about 100 mg for adult (as 60 kg body weight). For other animal species, the corresponding dose as converted per 60 kg body weight can be administered.

(2) Screening of Pharmaceutical Candidate Compound for Disease

Since the polypeptide of the present invention is present in vivo (especially in the cartilage tissue) as a humoral factor and has the function to suppress cartilage differentiation, a compound or its salt that promotes the function of the polypeptide of the present invention can be used as pharmaceuticals for the treatment/prevention of bone and joint diseases, e.g., arthritis deformans, chronic articular rheumatism, marble stone disease, etc., or pathological angiogenesis, etc.

On the other hand, a compound or its salt that inhibits the function of the polypeptide of the present invention can be used as pharmaceuticals for the treatment/prevention of diseases caused by over-production of the polypeptide of the present invention, for example, bone and joint diseases such as arthritis deformans, chronic articular rheumatism, osteogenesis imperfecta, oseteoporosis, bone fractures, osteonecrosis of the femoral head, chondrodysplasia, etc., or pathological angiogenesis, and the like.

Therefore, the polypeptide of the present invention is useful as reagents for screening the compound or its salt that promotes or inhibits the function of the polypeptide of the present invention.

That is, the present invention provides:

(1) a method for screening the compound or its salts that promote the function of the polypeptide of the present invention or its salts (hereinafter sometimes merely referred to as the accelerator), or the compound that inhibits the function of the polypeptide of the present invention or its salts (hereinafter sometimes merely referred to as the inhibitor), which comprises using the polypeptide of the present invention or its salts.

The kit for screening of the present invention comprises the polypeptide of the present invention or its salts.

The compound or its salts obtainable by the screening method or the screening kit of the present invention is the compound selected from, e.g., peptides, proteins, non-peptide compounds, synthetic compounds, fermentation products, cell extracts, plant extracts, animal tissue extracts, plasma, etc. and is the compound that promotes or inhibits the function of the polypeptide of the present invention.

As the salts of the compound, there may be employed similar salts to those of the polypeptide of the present invention described above.

When the compound or its salts obtainable by the screening method or the screening kit of the present invention are used as the therapeutic/prophylactic agents described above, a conventional means may be applied to making pharmaceutical preparations. For example, the compound or its salts may be prepared into tablets, capsules, elixirs, microcapsules, sterile solutions, suspensions, etc.

Since the thus obtained preparation is safe and low toxic, it can be administered orally or parenterally to human or warm-blooded animal (e.g., mouse, rat, rabbit, sheep, swine, bovine, horse, chicken, cat, dog, monkey, etc.).

The dose of the compound or salts thereof varies depending on activity, target disease, subject to be administered, method for administration, etc.; for example, when the compound that accelerates the function of the polypeptide of the present invention is orally administered for the treatment of bone and joint diseases, the dose is normally about 0.1 to about 100 mg, preferably about 1.0 to about 50 mg, more preferably about 1.0 to about 20 mg per day for adult (as 60 kg body weight). In parenteral administration, the single dose varies depending on subject to be administered, target disease, etc., but for the treatment of, e.g., bone and joint diseases, it is advantageous to administer the compound that accelerates the functions of the polypeptide of the present invention intravenously at a daily dose of about 0.01 to about 30 mg, preferably about 0.1 to about 20 mg, more preferably about 0.1 to about 10 mg for adult (as 60 kg body weight). For other animal species, the corresponding dose as converted per 60 kg weight can be administered.

Turning to the compound that inhibits the functions of the polypeptide of the present invention, when it is orally administered, the dose is normally about 0.1 to about 100 mg, preferably about 1.0 to about 50 mg, more preferably about 1.0 to about 20 mg per day for adult (as 60 kg body weight). In parenteral administration, the single dose varies depending on subject to be administered, target disease, etc. When the compound that inhibits the function of the polypeptide of the present invention is administered to adult (as 60 kg body weight) generally in the form of injection, it is advantageous to administer the compound intravenously at a daily dose of about 0.01 to about 30 mg, preferably about 0.1 to about 20 mg, more preferably about 0.1 to about 10 mg. For other animal species, the corresponding dose as converted per 60 kg weight can be administered.

(3) Quantification for the Polypeptide of the Present Invention or its Salts:

The antibody to the polypeptide of the present invention (hereinafter sometimes merely referred to as the antibody of the present invention) is capable of specifically recognizing the polypeptide of the present invention and thus, can be used for a quantification of the polypeptide of the present invention in a test sample fluid, in particular, for a quantification by sandwich immunoassay.

That is, the present invention provides:

(i) a method for quantification of the polypeptide of the present invention in a test sample fluid, which comprises competitively reacting the antibody of the present invention, a test sample fluid and a labeled form of the polypeptide of the present invention, and measuring the ratio of the labeled polypeptide of the present invention bound to said antibody, and, (ii) a method for quantification of the polypeptide of the present invention in a test sample fluid, which comprises reacting the test sample fluid simultaneously or continuously with the antibody of the present invention immobilized on a carrier and a labeled form of the antibody of the present invention, and then measuring the activity of the labeling agent on the insoluble carrier.

The monoclonal antibody to the polypeptide of the present invention (hereinafter sometimes simply referred to as the monoclonal antibody of the present invention) may be used to quantify the polypeptide of the present invention. Moreover, the polypeptide of the present invention can be detected by means of a tissue staining as well. For these purposes, the antibody molecule per se may be used or F(ab')$_2$, Fab' or Fab fractions of the antibody molecule may also be used.

There is no particular limitation for the quantification method using the antibody of the present invention to the polypeptide of the present invention; any method is usable so far as it relates to a method in which the amount of antibody, antigen or antibody-antigen complex can be detected by a chemical or a physical means, corresponding to the amount of antigen (e.g., the amount of the polypeptide of the present invention) in a test sample fluid to be detected, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of the labeling agent used in the assay method using the labeling substance are radioisotopes, enzymes, fluorescent substances and luminescent substances, etc. Examples of the radioisotope are $[^{125}I]$, $[^{131}I]$, $[^{3}H]$, $[^{14}C]$, etc. Preferred examples of the enzyme are those that are stable and have a high specific activity, which include □-galactosidase, □-glucosidase, alkaline phosphatase, peroxidase, malate dehydrogenase, etc. Examples of the fluorescent substance are fluorescamine, fluorescein isothiocyanate, etc. Examples of the luminescent substance are luminol, a luminol derivative, luciferin, lucigenin, etc. Furthermore, the biotinavidin system may also be used for binding of an antibody or antigen to a labeling agent.

In the immobilization of antigens or antibodies, physical adsorption may be used. Alternatively, chemical binding that is conventionally used for immobilization of proteins or enzymes may be used as well. Examples of the carrier include insoluble polysaccharides such as agarose, dextran and cellulose; synthetic resins such as polystyrene, polyacrylamide and silicone; glass; etc.

In the sandwich method, a test sample fluid is reacted with an immobilized monoclonal antibody of the present invention (first reaction), then reacted with another labeled monoclonal antibody of the present invention (second reaction) and the activity of the labeling agent on the insoluble carrier is assayed, whereby the amount of the polypeptide of the present invention in the test sample fluid can be quantified. The first and second reactions may be carried out in a reversed order, simultaneously or sequentially with an interval. The type of the labeling agent and the method for immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the measurement sensitivity, etc.

In the method for assaying the polypeptide of the present invention by the sandwich method according to the present invention, preferred monoclonal antibodies of the present invention used for the first and the second reactions are antibodies, which binding sites to the polypeptide of the present invention are different from one another. Thus, the antibodies used in the first and the second reactions are those wherein, when the antibody used in the second reaction recognizes the C-terminal region of the polypeptide of the present invention or the receptor protein, the antibody recognizing the site other than the C-terminal regions, e.g., recognizing the N-terminal region, is preferably used in the first reaction.

The monoclonal antibody of the present invention may be used in an assay system other than the sandwich method, such as a competitive method, an immunometric method and a nephrometry.

In the competitive method, an antigen in a test sample fluid and a labeled antigen are competitively reacted with an antibody, then the unreacted labeled antigen (F) and the labeled antigen bound to the antibody (B) are separated (i.e., B/F separation) and the labeled amount of either B or F is measured to determine the amount of the antigen in the test sample fluid. In the reactions for such a method, there are a liquid phase method in which a soluble antibody is used as the antibody and the B/F separation is effected by polyethylene glycol while a second antibody to the antibody is used, and a solid phase method in which an immobilized antibody is used as the first antibody or a soluble antibody is used as the first antibody while an immobilized antibody is used as the second antibody.

In the immunometric method, an antigen in a test sample fluid and an immobilized antigen are competitively reacted with a given amount of a labeled antibody followed by separating the solid phase from the liquid phase; or an antigen in a test sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the test sample fluid.

In the nephrometry, the amount of insoluble sediment, which is produced as a result of the antigen-antibody reaction in a gel or in a solution, is measured. Even when the amount of an antigen in a test sample fluid is small and only a small amount of the sediment is obtained, a laser nephrometry utilizing laser scattering can be suitably used.

In applying each of those immunoassays to the assay method for the present invention, any special conditions or operations are not required to set forth. The assay system for the polypeptide of the present invention may be constructed in addition to conditions or operations conventionally used for each of the methods, taking the technical consideration of one skilled in the art into account consideration. For the details of such conventional technical means, a variety of reviews, reference books, etc. may be referred to.

Reference may be made to, for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by lgaku Shoin, 1982); Eiji Ishikawa, et al. (ed.): "Enzyme Immunoassay" (Third Edition) (published by Igaku Shoin, 1987); "Methods in Enzymology" Vol. 70 (Immuochemical Techniques (Part A)); ibid;, Vol: 73.(Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part 1: Hybridoma Technology and Monoclonal Antibodies)) (published by Academic Press); etc.)

As described above, the polypeptide of the present invention can be quantified with high sensitivity, using the antibody of the present invention.

Furthermore, by quantifying the level of the polypeptide of the present invention using the antibody of the present invention, (1) when an increase in level of the polypeptide of the present invention is detected, it can be diagnosed that the following diseases are involved or it is highly suspected of these disease to occur in the future. Examples of such diseases are bone and joint diseases (e.g., arthritis deformans, chronic articular rheumatism, osteogenesis imperfecta, oseteoporosis, bone fractures, osteonecrosis of the femoral head, chondrodysplasia, etc.) and pathological angiogenesis (e.g., tumor angiogenesis, etc.). Also, (2) when a decrease in level of the polypeptide of the present invention is detected, it can be diagnosed that the following diseases are involved or it is highly suspected of these disease to be caused in the future. Examples of such diseases are bone and joint diseases (e.g., arthritis deformans, chronic articular rheumatism, marble stone disease, etc.) and pathological angiogenesis (e.g., tumor angiogenesis, etc.).

The antibody of the present invention can be employed for detecting the polypeptide of the present invention which may be present in a test sample fluid such as a body fluid, a tissue, etc. The antibody can also be used for the preparation of an antibody column to purify the polypeptide of the present invention, detect the polypeptide of the present invention in each fraction upon purification, and analysis of the behavior of the polypeptide of the present invention in the cells under inspection.

(4) Gene Diagnostic Agent

By using the DNA of the present invention, e.g., as a probe, an abnormality (gene abnormality) of the DNA or mRNA encoding the polypeptide of the present invention in human or other warm-blooded animal (e.g., rat, mouse, guinea pig, rabbit, chicken, sheep, swine, bovine, horse, cat, dog, monkey, etc.)can be detected. Therefore, the DNA of the present invention is useful as a gene diagnostic agent for the damage to the DNA or mRNA, its mutation, or its decreased expression, or increased expression or overexpression of the DNA or mRNA.

The gene diagnosis described above using the DNA of the present invention can be performed by, for example, the publicly known Northern hybridization assay or the PCR-SSCP assay (Genomics, 5, 874–879 (1989); Proceedings of the National Academy of Sciences of the United. States of America, 86, 2766–2770 (1989)); a DNA micro array, etc.

In case that decreased expression or overexpression is detected by, e.g., the Northern hybridization or a DNA micro array, or mutation of the DNA is detected by the PCR-SSCP method or a DNA micro array, it can be diagnosed that the following diseases are involved or it is highly likely to suffer from these disease in the future. Examples of such diseases are bone and joint diseases (e.g., arthritis deformans, chronic articular rheumatism, marble stone disease, etc.) and pathological angiogenesis (e.g., tumor angiogenesis, etc.).

(5) Pharmaceutical Comprising Antisense DNA

Antisense DNA that binds complemenarily to the DNA of the present invention to inhibit expression of the DNA can be used as the agent for the treatment prevention of diseases that are caused by in vivo overexpression of the polypeptide of the present invention or the DNA of the present invention (e.g., bone and joint diseases such as arthritis deformans, chronic articular rheumatism, osteogenesis imperfecta, oseteoporosis, bone fractures, osteonecrosis of the femoral head, chondrodysplasia, etc., or pathological angiogenesis such as tumor angiogenesis, etc.).

The antisense DNA described above can be used for the therapeutic/prophylactic agent described above, as in the therapeutic/prophylactic agent of various diseases comprising the DNA of the present invention described above.

For example, the antisense DNA is administered directly, or the antisense DNA is inserted into an appropriate vector such as retrovirus vector, adenovirus vector, adenovirus-associated virus vector, etc. followed by treating in a conventional manner. The antisense DNA may be administered as it stands, or with a physiologically acceptable carrier to assist its uptake by gene gun or through a catheter such as a catheter with a hydrogel.

In addition, the antisense DNA may also be employed as an oligonucleotide probe for diagnosis to examine the presence of the DNA of the present invention in tissues or cells and states of its expression.

(6) Pharmaceutical Comprising the Antibody of the Present Invention

The antibody of the present invention which possesses the effect to neutralize the activities of the polypeptide of the present invention can be used as pharmaceuticals for the treatment/prevention of diseases that are caused by in vivo overexpression of the polypeptide of the present invention or the DNA of the present invention (e.g., bone and joint diseases such as arthritis deformans, chronic articular rheumatism, osteogenesis imperfecta, oseteoporosis, bone fractures, osteonecrosis of the femoral head, chondrodysplasia, etc., or pathological angiogenesis such as tumor angiogenesis, etc.).

The agent comprising the antibody of the present invention for the treatment and prevention of the aforesaid diseases may be administered orally or parenterally to human or mammal (e.g., rat, rabbit, sheep, swine, bovine, cat, dog, monkey, etc.) as a liquid preparation in its original form, or as a pharmaceutical composition in an appropriate pharmaceutical formulation. The dose varies depending on subject to be administered, target disease, conditions, route for administration, etc.; for example, when used for the treatment of bone and joint disease, the antibody of the present invention is intravenously administered normally in the dose of about 0.01 mg to about 20 mg/kg body weight, preferably about 1.0 to about 10 mg/kg body weigh, and more preferably about 0.1 to about 5 mg per day once to about 5 times a day, preferably once to about 3 times. In parenteral administration via other route and in oral administration, a dose similar to those given above can be administered. Where conditions are serious, the dose may be increased depending on the conditions.

The antibody of the present invention may be administered in itself or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets); pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections. Such injections are prepared by publicly known methods, e.g., by dissolving, suspending or emulsifying the aforesaid antibody or its salts in a sterile aqueous or oily liquid medium. For the aqueous medium for injection, for example, physiological saline and isotonic solutions containing glucose and other adjuvant, etc. are used. Appropriate dissolution aids, for example, alcohol (e.g., ethanol), polyalcohol (e.g., propylene glycol, polyethylene glycol), nonionic surfactant [e.g., polysorbate 80™, HCO-50 (polyoxyethylene (50 mol) adduct of hydrogenated castor oil)] may be used in combination. For the oily solution, for example, sesame oil, soybean oil and the like are used, and dissolution aids such as benzyl benzoate and benzyl alcohol may be used in combination. The thus-prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of about 5 to about 500 mg per unit dosage form, about 5 to about 100 mg especially for injections and about 10 to about 250 mg for other preparations.

Each composition described above may further contain other active components unless formulation with the antibody causes any adverse interaction.

(7) DNA Transgenic Animal

The present invention provides a non-human mammal bearing DNA encoding the polypeptide of the present invention, which is exogenous (hereinafter abbreviated as the exogenous DNA of the present invention) or its variant DNA (sometimes merely referred to as the exogenous variant DNA of the present invention).

Thus, the present invention provides:

(1) a non-human mammal bearing the exogenous DNA of the present invention or its variant DNA;

(2) the mammal according to (1), wherein the non-human mammal is a rodent;

(3) the mammal according to (2), wherein the rodent is mouse or rat; and, (4) a recombinant vector bearing the exogenous DNA of the present invention or its variant DNA and capable of expressing in a mammal.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to prepare the transgenic animal of the present invention.

Examples of the non-human mammal that can be used include bovine, swine, sheep, goats, rabbits, dogs, cats, guinea pigs, hamsters, mice, rats, and the like. Above all, preferred are rodents, especially mice (e.g., C57B1/6 strain, DBA2 strain, etc. for a pure line and for a cross line, B6C3F$_1$ strain, BDF$^1$ strain B6D2F$_1$ strain, BALB/c strain, ICR strain, etc.) or rats (Wistar, SD, etc.), since they are relatively short in ontogeny and life cycle from a standpoint of preparing model animals for human disease.

"Mammals" in a recombinant vector that can be expressed in the 20 mammals include the aforesaid non-human mammals and human.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean the DNA that expresses a polypeptide and exemplified by the DNA capable of expressing a polypeptide that suppresses the function of the normal polypeptide of the present invention.

The exogenous DNA of the present invention may be any one of those derived from a mammal of the same species as, or a different species from, the mammal as the target animal. In transfecting the DNA of the present invention, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highlyhomologous to the human DNA.

As expression vectors for the polypeptide of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (1) promoters for DNA derived from viruses (e.g., simian virus, cytomegalovirus, Moloney leukemia virus, JC virus, breast cancer virus, poliovirus, etc.), and (2) promoters derived from various mammals (human, rabbits, dogs, cats, guinea pigs, hamsters, rats, mice, etc.), for example, promoters of albumin, insulin 11, uroplakin 11, elastase, erythropoietin, endothelin, muscular creatine kinase, glial fibrillary acidic protein, glutathione S-transferase, platelet-derived growth factor □, keratins K1, K10 and K14, collagen types I and II, cyclic AMP-dependent protein kinase □I subunit, dystrophin, tartarate-resistant alkaline phosphatase, atrial natriuretic factor, endothelial receptor tyrosine kinase (generally abbreviated as Tie2), sodium-potassium adenosine triphosphorylase (Na, K-ATPase), neurofilament light chain, metallothioneins I and IIA, metalloproteinase I tissue inhibitor, MHC class I antigen.(H-2L), H-ras, renin, dopamine □-hydroxylase, thyroid peroxidase (TPO), polypeptide chain elongation factor 1□ (EF-1□), □ actin, □ and □ myosin heavy chains, myosin light chains 1 and 2, myelin base protein, thyroglobulins, Thy-1, immunoglobulins, H-chain variable region (VNP), serum amyloid component P, myoglobin, troponin C, smooth muscle ☐ actin, preproencephalin A, vasopressin, etc. Among them, cytomegalovirus promoters, human polypeptide elongation factor 1☐ (EF1☐) promoters, human and chicken ☐ actin promoters etc., which protein can highly express in the whole body, are preferred.

It is preferred that the vectors described above have a sequence for terminating the transcription of the desired messenger RNA in the DNA transgenic animal (generally termed a terminator); for example, a sequence of each DNA derived from viruses and various mammals. SV40 terminator of the simian virus, etc. are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region can be prepared by a conventional DNA engineering technique in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the animal prepared will maintain the exogenous DNA of the present invention in all of the germinal cells and somatic cells thereof. The offspring of the animal that inherits the exogenous DNA of the present invention also have the exogenous DNA in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the exogenous DNA of the present invention is excessively present in all of the germinal cells and somatic cells thereof. The offspring of the animal that inherits the exogenous DNA of the present invention have excessively the exogenous DNA of the present invention in all of the germinal cells and somatic cells thereof.

By obtaining a homozygotic animal having the transfected DNA in both of homologous chromosomes and mating a male and female of the animal, all offspring can be passaged to retain the DNA.

In a non-human mammal bearing the normal DNA of the present invention, the normal DNA of the present invention has expressed to a high level, and may eventually develop hyperfunction in the function of the polypeptide of the present invention by promoting the function of endogenous normal DNA. Therefore, the animal can be utilized as a pathologic model animal for such a disease. Specifically, using the normal DNA transgenic animal of the present invention, it is possible to elucidate the mechanism of hyperfunction in the function of the polypeptide of the present invention and the pathological mechanism of the disease associated with the polypeptide of the present invention and to determine how to treat these diseases.

Furthermore, since a mammal transfected with the exogenous normal DNA of the present invention exhibits an increasing symptom of the polypeptide of the present invention librated, the animal is usable for screening of treatment agent for the disease associated with the polypeptide of the present invention.

On the other hand, non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfection of the abnormal DNA of the present invention at the fertilized egg cell stage is preserved to be present in all of the germinal and somatic cells of the mammals to be subjected. The fact that the abnormal DNA of the present invention is present in the germinal cells of the animal after DNA transfection means that all of the offspring of the prepared animal have the abnormal DNA of the present invention in all of the germinal and somatic cells. Such an offspring that passaged the exogenous DNA of the present invention contains the abnormal DNA of the present invention in all of the germinal and somatic cells. A homozygous animal having the introduced DNA on both of homologous chromosomes can be acquired, and then by mating these male and female animals, all the offspring can be bled to have the DNA.

Since non-human mammal having the abnormal DNA of the present invention may express the abnormal DNA of the present invention at a high level, the animal may eventually be the function inactivation type inadaptability of the polypeptide of the present invention by inhibiting the function of the endogenous normal DNA and can be utilized as its disease model animal. For example, using animal transfected with the abnormal DNA of the present invention, it is possible to elucidate the mechanism of inadaptability of the polypeptide and to perform studies on a method for treatment of this disease.

More specifically, the transgenic animal of the present invention expressing the abnormal DNA of the present invention at a high level is also expected to serve as an experimental model for the elucidation of the mechanism of the functional inhibition (dominant negative effect) of a normal polypeptide by the abnormal polypeptide of the present invention in the function inactive type inadaptability of the polypeptide of the present invention.

A mammal bearing the abnormal exogenous DNA of the present invention is also expected to serve for screening a candidate drug for the treatment of the function inactive type inadaptability of the polypeptide of the present invention, since a free form of the polypeptide of the present invention is increased in such an animal.

Other potential applications of two kinds of the transgenic animals described above include:

(1) use as a cell source for tissue culture;
(2) elucidation of the relation to a polypeptide that is specifically expressed or activated by the polypeptide of the present invention, through direct analysis of the DNA or RNA in tissue of the DNA transgenic animal of the present invention or through analysis of the polypeptide tissue expressed by the DNA;
(3) research on the function of cells derived from tissues that are cultured usually only with difficulty, using cells of tissue bearing the DNA cultured by a standard tissue culture technique;

(4) screening of a drug that enhances cell functions using the cells described in (3) above; and, (5) isolation and purification of the variant polypeptide of the present invention and preparation of an antibody thereto.

Furthermore, clinical conditions of a disease associated wit the polypeptide of the present invention, including the function inactive type inadaptability of the polypeptide of the present invention can be determined using the DNA transgenic animal of the present invention. Also, pathological findings on each organ in a disease model associated with the polypeptide of the present invention can be obtained in more detail, leading to the development of a new method for treatment as well as the research and therapy of any secondary diseases associated with the disease.

It is also possible to obtain a free DNA-transfected cell by removing each organ from the DNA transgenic animal of the present invention, mincing the organ and degrading with a polypeptide (protein) degrading enzyme such as trypsin, etc., followed by establishing the line of culturing or cultured cells. Furthermore, the DNA transgenic animal of the present invention can serve as identification of cells capable of producing the polypeptide of the present invention, and as studies on relevance to apoptosis, differentiation or propagation, or on the mechanism of signal transduction in these properties to inspect any abnormality therein. Thus, the DNA transgenic animal of the present invention can provide an effective research material for the polypeptide of the present invention and for elucidating its function and effect.

To develop a therapeutic drug for the treatment of diseases associated with the polypeptide of the present invention, including the function inactive type inadaptability of the polypeptide of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the polypeptide of the present invention, using the DNA transgenic animal of the present invention or a vector capable of expressing the exogenous DNA of the present invention.

(8) Knockout Animal

The present invention provides a non-human mammal embryonic stem cell bearing the DNA of the present invention inactivated and a non-human mammal deficient in expressing the DNA of the present invention.

Thus, the present invention provides:

(1) a non-human embryonic stem cell in which the DNA of the present invention is inactivated;

(2) the embryonic stem cell according to (1), wherein the DNA is inactivated by introducing a reporter gene (e.g., □-galactosidase gene derived from *Escherichia coli*);

(3) the embryonic stem cell according to (1), which is resistant to neomycin;

(4) the embryonic stem cell according to (1), wherein the non-human mammal is a rodent;

(5) the embryonic stem cell according to (4), wherein the rodent is mouse;

(6) a non-human mammal deficient in expressing the DNA, wherein the DNA of the present invention is inactivated;

(7) the non-human mammal according to (6), wherein the DNA is inactivated by inserting a reporter gene (e.g., □-galactosidase derived from *Escherchia coli*) therein and the reporter gene is capable of being expressed under control of a promoter for the DNA of the present invention;

(8) the non-human mammal according to (6), wherein the nonhuman mammal is a rodent;

(9) the non-human mammal according to claim 8, wherein the rodent is mouse; and,

(10) a method for screening a compound or its salt that promotes or inhibits the activity of a promoter to the DNA of the present invention, which comprises administering a test compound to the mammal of (7) and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the polypeptide of the present invention (hereinafter sometimes referred to as the knockout DNA of the present invention) by substantially inactivating the activities of the polypeptide of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (□-galactosidase gene) or cat (chloramphenicol acetyltransferase gene), etc. into its exon site thereby to disable the functions of exon, or integrating to a chromosome of the subject animal by, e.g., homologous recombination, a DNA sequence which terminates gene transcription (e.g., polyA additional signal, etc. in the intron between exons to, thus inhibit the synthesis of complete messenger RNA and eventually disrupt the gene (hereinafter simply referred to as targeting vector). The thus-obtained ES cells are subjected to the Southern hybridization analysis with a DNA sequence on or near the DNA of the present invention as a probe, or to PCR analysis with a DNA sequence on the targeting vector and another DNA sequence near the DNA of the present invention, which is not included in the targeting vector as primers, thereby to select the knockout ES cell of the present invention.

The parent ES cells to inactivate the DNA of the present invention by homologous recombination, etc. may be of a strain already established as described above, or may be originally established in accordance with a modification of the known method by Evans and Kaufman supra. For example, in the case of mouse ES cells, currently it is common practice to use ES cells of the 129 strain. However, since their immunological background is obscure, the C57BL/6 mouse or the BDF1 mouse (F1 hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The BDF1 mouse is advantageous in that, when a pathologic model mouse is generated using ES cells obtained therefrom, the genetic background can be changed to that of the C57BL/6 mouse by backcrossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is also desirable that sexes be identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about 106 cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and about 90% air) in the presence of LIF (1–10000 U/ml) on appropriate feeder cells such as STO fibroblasts, treated with a trypsin/EDTA solution (normally approximately 0.001–0.5% trypsin/approximately 0.1–5 mM EDTA, preferably about 0.1% trypsin/about 1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

Where ES cells are allowed to reach a high density in mono-layers or to form cell aggregates in suspension under appropriate conditions, they will spontaneously differentiate to various cell types, for example, parietal and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtainable from the differentiated ES cells of the present invention are useful for studying the function of the polypeptide of the present invention cytologically or molecular biologically.

The non-human mammal deficient in expression of the DNA of the present invention can be distinguished from a normal animal by measuring the mRNA amount in the subject animal by a publicly known method, and indirectly comparing the degree of expression.

As the non-human mammal, the same examples supra apply.

With respect to the non-human mammal deficient in expression of the DNA of the present invention, the DNA of the present invention can be made knockout by transfecting a targeting vector, prepared as described above, to mouse embryonic stem cells or mouse oocytes, and conducting homologous recombination in which a targeting vector DNA sequence, wherein the DNA of the present invention is inactivated by the transfection, is replaced with the DNA of the present invention on a chromosome of a mouse embryonic stem cell or mouse embryo.

The knockout cells with the DNA of the present invention disrupted can be identified by the Southern hybridization analysis with a DNA fragment on or near the DNA of the present invention as a probe, or by PCR analysis using as primers a DNA sequence on the targeting vector and another DNA sequence of the mouse-derived DNA of the present invention, which is not included in the targeting vector. When non-human mammalian embryonic stem cells are used, a cell line wherein the DNA of the present invention is inactivated by homologous recombination is cloned; the resulting cloned cell line is injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the polypeptide of the present invention. The individuals deficient in homozygous expression of the polypeptide of the present invention can be obtained from offspring of the intercross between the heterozygotes.

When an oocyte or egg cell is used, a DNA solution may be injected, e.g., to the prenucleus by microinjection thereby to obtain a transgenic non-human mammal having a targeting vector introduced in a chromosome thereof. From such transgenic non-human mammals, those having a mutation at the locus of the DNA of the present invention can be obtained by selection based on homologous recombination.

As described above, individuals in which the DNA of the present invention is rendered knockout permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell in which the DNA of the present invention is inactivated is very useful for preparing a non-human mammal deficient in expression of the DNA of the present invention.

Since the non-human mammal in which the DNA of the present invention is deficiently expressed lacks various biological activities induced by the polypeptide of the present invention, such an animal can be a disease model suspected of inactivated biological activities of the polypeptide of the present invention and thus, offers an effective study to investigate causes for and therapy for these diseases.

(8a) Method for screening of compounds that are effective for the treatment/prevention of diseases caused by deficiency, damages, etc. of the DNA of the present invention.

The non-human mammal deficient in expression of the DNA of the present invention can be employed for screening of compounds that are effective for the treatment/prevention of diseases caused by deficiency, damages, etc. of the DNA of the present invention.

That is, the present invention provides a method for screening of a compound having therapeutic/prophylactic effects for diseases caused by deficiency, damages, etc. of the DNA of the present invention, which comprises administering a test compound to the non-human mammal deficient in expression of the DNA of the present invention and observing/measuring a change occurred in the animal.

As the non-human mammal deficient in expression of the DNA of the present invention which can be employed for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma and the like and these compounds may be novel compounds or publicly known compounds.

Specifically, the non-human mammal deficient in expression of the DNA of the present invention is treated with a test compound, comparison is made with an intact animal for control and a change in each organ, tissue, disease conditions, etc. of the animal is used as an index to assess the therapeutic/prophylactic effects of the test compound.

For treating a test animal with a test compound, for example, oral administration, intravenous injection, etc. are available, and the treatment is appropriately selected depending upon conditions of the test animal, properties of the test compound, etc. Furthermore, an amount of administration for a test compound can be appropriately chosen depending on the administration route, nature of the test compound and the like.

In the case of screening a compound effective for the treatment/prevention of, e.g., tumor angiogenesis, a cancer cell is transplanted to the non-human mammal deficient in expression of the DNA of the present invention, a test compound is administered before or after the cancer cell transplantation and, a tumor marker value, tumor mass size, etc. of the animal is measured with passage of time.

The compound obtainable using the above screening method is a compound selected from the test compounds described above and exhibits a therapeutic and prophylactic effect for the diseases caused by deficiencies, damages, etc. of the polypeptide of the present invention (bone and joint diseases (e.g., arthritis deformans, chronic articular rheumatism, marble stone disease, etc.), pathological angiogenesis (e.g., tumor angiogenesis), etc.). Therefore, the compound can be employed as: a safe and low toxic pharmaceutical such as an agent for the treatment and prevention of these diseases. Furthermore, compounds derived from such a compound obtainable by the screening supra can be employed as well.

The compound obtained by the screening above may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A pharmaceutical comprising the compound obtained by the above screening method or salts thereof may be manufactured in a manner similar to the method for preparing the pharmaceutical comprising the polypeptide of the present invention described hereinabove.

Since the pharmaceutical thus obtained is safe and low toxic, it can be administered to human and another mammal (e.g., rat, mouse, guinea pig, rabbit, sheep, swine, bovine, horse, cat, dog, monkey, etc.).

The dose of the compound or its salt to be administered varies depending upon particular disease, subject to be administered, route of administration, etc., but when it is orally administered to an adult (as 60 kg body weight) for the treatment of bone and joint disease, the compound is administered generally in a dose of about 0.1 mg/day to about 100 mg/day, preferably about 1.0 mg/day to about 50 mg/day, more preferably about 1.0 mg/day to about 20 mg/day. When it is parenterally administered to an adult (as 60 kg body weight) for the treatment of bone and joint disease, the single dose of the compound varies depending upon subject to be administered, particular disease, etc., and it is advantageous to administer the composition in the form of an injectable preparation in a dose of about 0.01 mg/day to about 30 mg/day, preferably about 0.1 mg/day to about 20 mg/day, more preferably about 0.1 mg/day to about 10 mg/day. As for other animals, the composition can be administered in the above dose with converting it into that for the body weight of 60 kg.

(8b) Method for screening a compound or its salt that promotes or inhibits the activities of a promoter to the DNA of the present invention The present invention provides a method for screening a compound or its salt that promotes or inhibits the activities of a promoter to the DNA of the present invention, which comprises administering a test compound to a non-human mammal deficient in expression of the DNA of the present invention and detecting expression of the reporter gene.

In the screening method supra, the non-human mammal deficient in expression of the DNA of the present invention is selected from the 20 aforesaid non-human mammal deficient in expression of the DNA of the present invention, as an animal in which the DNA of the present invention is inactivated by introducing a reporter gene and the reporter gene is expressed under control of a promoter to the DNA of the present invention.

The same examples of the test compound described above apply to specific test compounds.

As the reporter gene, the same specific examples apply to those for this method. Preferably employed are □-galactosidase (lacZ), soluble alkaline phosphatase gene, luciferase gene and the like.

Since a reporter gene is present under control of a promoter to the DNA of the present invention in the non-human mammal deficient in expression of the DNA of the present invention wherein the DNA of the present invention is substituted with the reporter gene, the activity of the promoter can be detected by tracing expression of a substance encoded by the reporter gene.

When a part of the DNA region encoding the polypeptide of the present invention is substituted with, e.g., □-galactosidase gene (lacZ) derived from *Escherichia coli*, □-galactosidase is expressed in a tissue where the polypeptide of the present invention should originally be expressed, instead of the polypeptide of the present invention. Thus, the state of expression of the polypeptide can be readily observed in vivo of an animal by staining with a reagent, e.g., 5-bromo-4-chloro-3-indolyl-□-D-galactopyranoside (X-gal) which is a substrate for □-galactosidase. Specifically, a mouse deficient in the polypeptide of the present invention, or its tissue section is fixed with glutaraldehyde, etc. After washing with phosphate buffered saline (PBS), the system is reacted with abstaining solution containing X-gal at room temperature or about 37° C. for approximately 30 minutes to an hour. After the □-galactosidase reaction is terminated by washing the tissue preparation with 1 mM EDTA/PBS solution, the color formed is observed. Alternatively, mRNA encoding lacZ may be detected in a conventional manner.

The compound or its salt obtainable by the screening method supra are compounds that are selected from the test compounds described above and that accelerate or inhibit the activity of a promoter to the DNA of the present invention.

The compound obtained by the screening method above may take the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Since the compound or its salt that promotes or inhibits the activity of a promoter to the DNA of the present invention can accelerate the expression of the polypeptide of the present invention or can accelerate the function of the polypeptide of the present invention, they are useful as safe and low toxic pharmaceuticals for the treament/prevention of diseases, for example, bone and joint diseases (e.g., arthritis deformans, chronic articular rheumatism, marble stone disease, etc.), pathological angiogenesis (e.g., tumor angiogenesis), etc.

In addition, compounds derived from the compounds obtained by the screening supra can be used as well.

The pharmaceutical composition comprising the compound or its salt obtained by the screening method can be manufactured as in the pharmaceutical comprising the polypeptide of the present invention or its salt, described above.

The thus obtained pharmaceutical is safe and low toxic, and can thus be administered to, e.g., human or mammal (e.g., rat, mouse, guinea pig, rabbit, sheep, swine, bovine, horse, cat, dog, monkey, etc.).

The dose of the compound or its salt varies depending on target disease, subject to be administered, route for administration, etc.; for example, in oral administration of the compound that promotes the activity of a promoter to the DNA of the present invention for the treatment of, e.g., bone and joint diseases, the dose is normally about 0.1 to about 100 mg, preferably about 1.0 to about 50 mg, more preferably about 1.0 to about 20 mg per day for adult (as 60 kg body weight). In parenteral administration, the single dose varies depending on subject to be administered, target disease, etc. but it is advantageous to administer, for example, the compound that accelerates the activity of a promoter to the DNA of the present invention intravenously at a daily dose of about 0.01 to about 30 mg, preferably about 0.1 to about 20 mg, more preferably about 0.1 to about 10 mg for adult (as 60 kg body weight). For other animal species, the corresponding dose as converted per 60 kg weight can be administered.

On the other hand, when the compound that inhibits the activity of a promoter to the DNA of the present invention is orally administered, the dose is normally from about 0.1 to about 100 mg, preferably about 1.0 to about 50 mg, more preferably about 1.0 to about 20 mg per day for adult (as 60 kg body weight). In parenteral administration, the single dose varies depending on subject to be administered, target disease, etc. When the compound that inhibits the activity of a promoter to the DNA of the present invention is administered to an adult (as 60 kg body weight) generally in the form of injection, it is advantageous to administer the compound intravenously at a daily dose of about 0.01 to about 30 mg, preferably about 0.1 to about 20 mg, more preferably about 0.1 to about 10 mg. For other animal species, the corresponding dose as converted per 60 kg weight can be administered.

As stated above, the non-human mammal deficient in expression of the DNA of the present invention is extremely useful for screening the compound or its salt that promotes or inhibits the activity of a promoter to the DNA of the present invention and can greatly contribute to the elucidation of causes for various diseases suspected of deficiency in expression of the DNA of the present invention and for the development of pharmaceuticals for the prevention/treatment of these diseases.

In addition, extremely large quantities of the gene encoding the polypeptide of the present invention are expressed in mouse or human, especially in the cartilage tissue. Thus, the promoter sequence of the gene is advantageously used as a promoter to express a protein of interest (an optional useful gene product, etc.) in the cartilage tissue of a non-human warm-blooded animal. Specific examples of the warm blooded animal are the same as those given above.

That is, the present invention provides a method of expressing an protein of interest (an optional useful gene product, etc.) predominantly in the cartilage tissue of a non-human warm blooded animal, which comprises ligating the protein of interest (an optional useful gene product, etc.) to the gene encoding the polypeptide comprising the amino acid sequence represented by SEQ ID NO:6, SEQ ID NO:12 or SEQ ID NO:47 at the downstream of its promoter region (3' terminal side) and inserting the protein into the non-human animal, Examples of the protein of interest (an optional useful gene product, etc.) include useful gene products such as cytokines (e.g., interleukin, interferon, chemokine, hematopoietic factors), growth factors (e.g., EGF (epidermal growth factor) or substances having an activity that is substantially the same as EGF (e.g., EGF, heregulin (HER2 ligand), etc.), insulin or substances having an activity that is substantially the same as insulin (e.g., insulin, IGF (insulin-like growth factor)-1, IGF-2, etc.), FGF (fibroblast growth factor) or substances having an activity that is substantially the same as FGF (e.g., aFGF, bFGF, KGF (Keratindcyte Growth Factor), HGF (Hepatocyte Growth Factor), FGF-10, etc.), other cell growth factors (e.g., CSF (colony stimulating factor), EPO (erythropoietin), IL-2 (interleukin-2), NGF (nerve growth factor), PDGF (platelet-derived growth factor), TGFP (transforming growth factor β)), etc.), hormones (e.g., lutenizing hormone-releasing hormone (LH-RH), growth hormone, growth hormone-releasing hormone (GH-RH), prolactin, melanocyte stimulating hormone, thyroid hormone-releasing hormone, thyroid-stimulating hormone, lutenizing hormone, corpus luteum hormone, follicle-stimulating hormone, gastrin, motilin, somatostatin, secretin, glucagon, PACAP, VIP, etc., digestive enzymes (e.g., amylase, pepsinogen, lipase, etc.), antibodies to pathogen (e.g., antibodies to pathogenic bacteria such as pathogenic Salmonella, etc., antibodies to pathogenic viruses such as influenza, etc., antibodies to parasites such as Echinococcus, etc., or the like), antibacterial polypeptides (e.g., cecropin, histatin, indolicidin, protegrin, defensin, lysozyme,etc.) and the like.

In the proteins of interest described above, (1) the cytokines are cartilage-specifically expressed, whereby, e.g., the immune activity of a non-human warm blooded animal can be potentiated or controlled; and, (2) the growth factors are cartilage-specifically expressed, whereby, e.g., the cartilage tissue of a non-human warm blooded animal can be protected, etc.

Hereinafter, the method of expressing an protein of interest (an optional useful gene product, etc.) predominantly in the cartilage tissue of a non-human warm blooded animal, which comprises ligating DNA or RNA encoding the protein of interest (an optional useful gene product, etc.) at the downstream of promoter region of the gene encoding the polypeptide comprising the amino acid sequence represented by SEQ ID NO:6, SEQ ID NO:12 or SEQ ID NO:47 (3' terminal side) and introducing it into the non-human animal, is described below more specifically.

First, the promoter of the gene encoding the polypeptide characterized by comprising the amino acid sequence represented by SEQ ID NO:6, SEQ ID NO:12 or SEQ ID NO:47 can be obtained by publicly known methods such as colony hybridization, plaque hybridization, PCR, etc. (e.g., methods described in Molecular Cloning, 2nd (J. Sambrook et al., Cold Spring Harbor Lab. Press, 1989), etc.). The region having the promoter activity can be identified by publicly known methods such as reporter assay, etc. (e.g., methods described in Analytical Biochemistry, vol. 188, page 245 (1990), etc.).

Next, in order to ligate a protein of interest (an optional useful gene product, etc.) at the downstream (3' terminal side) of the promoter obtained by the methods described above, the ligation can be performed by publicly known methods for constructing plasmids using T4 DNA ligase (e.g., methods described in Molecular Cloning, 2nd (J. Sambrook et al., Cold Spring Harbor Lab. Press, 1989), etc.).

For transfecting the promoter ligated with the DNA encoding the protein of interest (an optional useful gene product, etc.) at the downstream (3' terminal side) of the promoter, there are a method using electroporation, a method using gene gun, a method using a retroviral vector (a method described in, e.g., Blood Cells, 17, 407 (1991), etc.), a method using an adenoviral vector (a method described in, e.g., Pathology, 30, 335 (1998), etc.) or the like.

When bases, amino acids, etc. are shown by abbreviations in the specification and drawings, they are represented by the codes in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |

The substituents, protecting groups and reagents which are frequently used in the present specification are represented by the following symbols.

| | |
|---|---|
| Me | methyl group |
| Et | ethyl group |
| Bu | butyl group |
| Ph | phenyl group |
| Tc | thiazolidine-4(R)-carboxamide group |
| Tos | p-toluenesulfonyl |
| CHO | formyl |
| Bzl | benzyl |
| Cl$_2$—Bzl | 2,6-dichlorobenzyl |
| Bom | benzyloxymethyl |
| Z | benzyloxycarbonyl |
| Cl-Z | 2-chlorobenzyloxycarbonyl |
| Br-Z | 2-bromobenzyloxycarbonyl |
| Boc | t-butoxycarbonyl |
| DNP | dinitrophenol |
| Trt | trityl |
| Bum | t-butoxymethyl |

-continued

| Fmoc | N-9-fluorenylmethoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboximide |
| DCC | N,N'-dichlorohexylcarbodiimide |

The sequence identification numbers in the sequence listing of the specification indicates the following sequence, respectively.

[SEQ ID NO:1]
This shows the base sequence of the antisense strand primer used in EXAMPLE 1.

[SEQ ID NO:2]
This shows the base sequence of the sense strand primer used in EXAMPLE 1.

[SEQ ID NO:4]
This shows the base sequence of DNA encoding human MLP precursor bearing the amino acid sequence shown by SEQ ID NO:6.

[SEQ ID NO:5]
This shows the amino acid sequence of signal sequence contained in human MLP precursor bearing the amino acid sequence shown by SEQ ID NO:6.

[SEQ ID NO:6]
This shows the amino acid sequence of human MLP precursor.

[SEQ ID NO:7]
This shows the base sequence of the antisense strand primer used in EXAMPLE 2.

[SEQ ID NO:8]
This shows the base sequence of the sense strand primer used in EXAMPLE 2.

[SEQ ID NO: 10]
This shows the base sequence of DNA encoding mouse MLP precursor bearing the amino acid sequence shown by SEQ ID NO:12.

[SEQ ID NO: 11]
This shows the amino acid sequence of signal sequence contained in mouse MLP precursor bearing the amino acid sequence shown by SEQ ID NO:12.

[SEQ ID NO:12]
This shows the amino acid sequence of mouse MLP precursor.

[SEQ ID NO: 13]
This shows the base sequence of G3PDH-specific oligo DNA used in EXAMPLE 3.

[SEQ ID NO:14]
This shows the base sequence of G3PDH-specific oligo DNA used in EXAMPLE 3.

[SEQ ID NO:15]
This shows the base sequence of aggrecan-specific oligo DNA used in EXAMPLE 3.

[SEQ ID NO:16]
This shows the base sequence of aggrecan-specific oligo DNA used in EXAMPLE 3.

[SEQ ID NO:17]
This shows the base sequence of type II collagen-specific oligo DNA used in EXAMPLE 3.

[SEQ ID NO:18]
This shows the base sequence of type II collagen-specific oligo DNA used in EXAMPLE 3.

[SEQ ID NO:19]
This shows the base sequence of type X collagen-specific oligo DNA used in EXAMPLE 3.

[SEQ ID NO:20]
This shows the base sequence of type X collagen-specific oligo DNA used in EXAMPLE 3.

[SEQ ID NO:21]
This shows the base sequence of mouse MLP-specific oligo DNA used in EXAMPLE 3.

[SEQ ID NO:22]
This shows the base sequence of mouse MLP-specific oligo DNA used in EXAMPLE 3.

[SEQ ID NO:23]
This shows the base sequence of DNA encoding human MLP bearing the amino acid sequence shown by SEQ ID NO:24.

[SEQ ID NO:24]
This shows the amino acid sequence of human MLP.

[SEQ ID NO:25]
This shows the base sequence of DNA encoding mouse MLP bearing the amino acid sequence shown by SEQ ID NO:26.

[SEQ ID NO:26]
This shows the amino acid sequence of mouse MLP.

[SEQ ID NO:27]
This shows the base sequence of the primer employed in EXAMPLES 4 and 6.

[SEQ ID NO:28]
This shows the base sequence of the primer employed in EXAMPLE 4.

[SEQ ID NO:29]
This shows the base sequence of the cDNA fragment obtained in EXAMPLE 1.

[SEQ ID NO:30]
This shows the base sequence of the cDNA fragment obtained in EXAMPLE 2.

[SEQ ID NO:31]
This shows the amino acid sequence of the synthetic peptide employed in EXAMPLE 6.

[SEQ ID NO:32]
This shows the base sequence of oligo DNA used as the PCR primer in EXAMPLE 6.

[SEQ ID NO:33]
This shows the base sequence of oligo DNA used as the PCR primer in EXAMPLE 6.

[SEQ ID NO;34]
This shows the base sequence of oligo DNA used as the PCR primer in EXAMPLE 6.

[SEQ ID NO:35]
This shows the base sequence of oligo DNA used as the PCR primer in EXAMPLE 6.

[SEQ ID NO:36]
This shows the base sequence of oligo DNA used as the PCR primer in EXAMPLE 6.

[SEQ ID NO:37]
This shows the base sequence of oligo DNA used as the PCR primer in EXAMPLE 6.

[SEQ ID NO:38]
This shows the base sequence of oligo DNA used as the PCR primer in EXAMPLE 6.

[SEQ ID NO:39]
This shows the partial amino acid sequence of rat MLP precursor encoded by the DNA obtained in EXAMPLE 9.

[SEQ ID NO:40]
This shows the base sequence of the DNA encoding a part of rat MLP precursor obtained in EXAMPLE 9.

[SEQ ID NO:41]
This shows the base sequence of the DNA containing the DNA encoding a part of rat MLP precursor obtained in EXAMPLE 9.

[SEQ ID NO:42]

This shows the base sequence of oligo DNA used as the PCR primer in EXAMPLE 9.

[SEQ ID NO:43]

This shows the base sequence of oligo DNA used as the PCR primer in EXAMPLE 9.

[SEQ ID NO:44]

This shows the base sequence of oligo DNA used as the PCR primer in EXAMPLE 9.

[SEQ ID NO:45]

This shows the base sequence of oligo DNA used as the PCR primer in EXAMPLE 9.

[SEQ ID NO:46]

This shows the base sequence of the DNA encoding rat MLP precursor having the amino acid sequence represented by SEQ ID NO:47.

[SEQ ID NO:47]

This shows the amino acid sequence of rat MLP precursor.

[SEQ ID NO:48]

This shows the base sequence of the DNA encoding rat MLP having the amino acid sequence represented by SEQ ID NO:49.

[SEQ ID NO:49]

This shows the amino acid sequence of rat MLP.

[SEQ ID NO:50]

This shows the amino acid sequence of signal sequence contained in rat MLP precursor bearing the amino acid sequence shown by SEQ ID NO:47.

*Escherchia coli* transformant XL10-Gold/pDRL128vH obtained in EXAMPLE 1 later described has been deposited with the Ministry of International Trade and Industry, Agency of Industrial Science and Technology, National Institute of Bioscience and Human-Technology (NIBH), 1–3, Higashi 1-chome, Tsukuba-shi, Ibaraki-ken, Japan, under the Accession Number FERM BP-6750 since Jun. 25, 1999, and with Institute for Fermentation, Osaka (IFO), 17–85, Juso-honmachi 2-chome Yodogawa-ku, Osaka, Japan, as the Accession Number IFO 16292 since Jun. 25, 1999.

*Escherichia coli* transformant XL10-Gold/pDRL128vM obtained in EXAMPLE 2 later described has been deposited with the Ministry of International Trade and Industry, Agency of Industrial Science and Technology, National Institute of Bioscience and Human-Technology (NIBH), under the Accession Number FERM BP-6747 since Jun. 9, 1999, and with Institute for Fermentation (IFO), as the Accession Number IFO 16293 since Jun. 25, 1999.

*Escherichia coli* transformant XL10-Gold/pDRL128vR obtained in EXAMPLE 9 later described has been deposited with the Ministry of International Trade and Industry, Agency of Industrial Science and Technology, National Institute of Bioscience and Human-Technology (NIBH), under the Accession Number FERM BP-7167 since May 19, 2000, and with Institute for Fermentation (IFO) as the Accession Number IFO 16439 since May 26, 2000.

Hereinafter, the present invention is described in detail with reference to EXAMPLES, but not intended to limit the scope of the present invention thereto. The gene manipulation procedures using *Escherichia coli* were performed according to the methods described in the Molecular Cloning.

EXAMPLE 1

Cloning of cDNA Encoding Human MLP Precursor Protein

Cloning of CDNA encoding human MLP precursor protein was carried out by performing 5' RACE (Rapid Amplification of cDNA End) and 3' RACE using human fetal brain-derived poly(A)$^+$ RNA, according to the following procedures. From 1 μg of human fetal brain-derived poly (A)$^+$ RNA (Clonetech Inc.), 1st strand cDNA was synthesized using anchored primer having poly(T) following the restriction enzyme sites and Superscript II MMLV reverse transcriptase (Gibco BRL Inc.). Then, the anchored primer was added to the 1st strand cDNA at the 3' end using RNA ligase (Takara Shuzo Co., Ltd.). Next, 5' RACE was carried out using as an antisense strand primer the oligo DNA shown by SEQ ID NO:1, and 3' RACE was carried out using as a sense strand primer the oligo DNA shown by SEQ ID NO:2, whereby the 5' upstream sequence and the 3' downstream sequence starting from the respective primers were obtained, respectively. Base sequencing of each of the double stranded DNAs obtained indicates the presence of overlapping common sequences, which reveals that the two sequences are derived from the same gene. Therefore, the respective cDNA fragments obtained by 5' RACE and 3' RACE were ligated with the common sequence segment to finally obtain poly (A)$^+$-containing cDNA fragment of 923 base pairs (bp) in the full-length shown by SEQ ID NO:29. This cDNA fragment encoded a novel human MLP precursor protein of 128 amino acids represented by SEQ ID NO:6, containing a typical signal sequence of 18 amino acid residues shown by SEQ ID NO:5. This human MLP precursor protein had the highest homology to human MIA precursor protein, and the positions of four cysteine residues coincided (FIG. 1) but the homology between the two was only 23.4% on an amino acid level.

Plasmid pDRL128vH bearing the DNA encoding human MLP precursor protein obtained this EXAMPLE was transfected to *Escherichia coli* XL10-Gold to acquire transformant *Escherichia coli* XL10-Gold/pDRL128vH.

EXAMPLE 2

Cloning of cDNA Encoding Mouse MLP Precursor Protein

Figure 1:
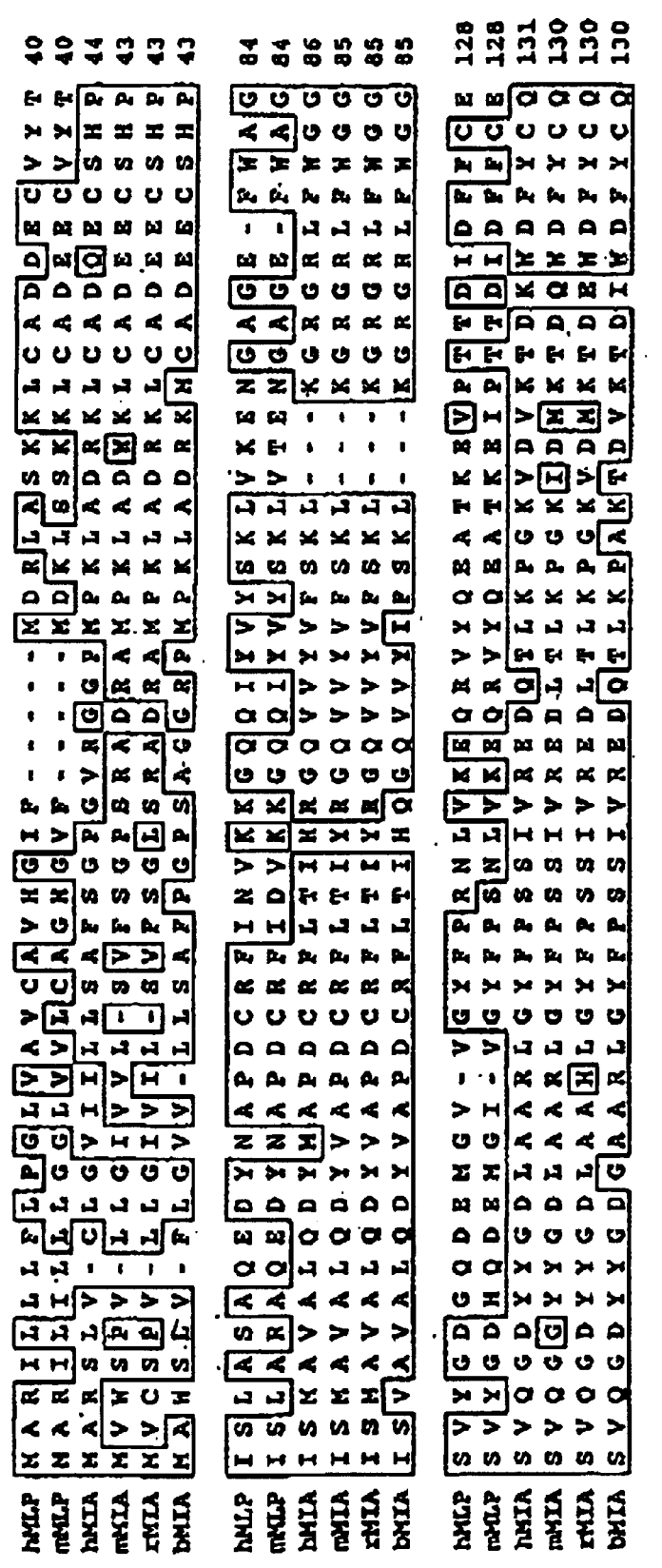

Cloning of CDNA encoding mouse MLP precursor protein was carried out by performing 5' RACE (Rapid Amplification of cDNA End) and 3' RACE, using poly(A)$^+$ RNA derived from the mouse fetus of 17.5 days old, as in the cloning of cDNA encoding human MLP precursor protein. After fractionation of the total RNA from the mouse fetus of 17.5 days old by the guanidine thiocyanate method, the total RNA was applied to oligo(dT) span column (Pharmacia) to prepare poly(A)$^+$ RNA. From 1 μg of poly(A)$^+$ RNA derived from the mouse fetus of 17.5 days old, 1st strand cDNA was synthesized using anchored primer having poly(T) following the restriction enzyme sites and Superscript II MMLV reverse transcriptase (Gibco BRL Inc.). Then, the anchored primer was added to the synthesized 1st strand cDNA at the 3' end, using RNA ligase (Takara Shuzo Co., Ltd.). The sequences of the primers used for 5' RACE and 3' RACE were prepared based on the sequence of AA222797, which was found in the public EST (Expressed Sequence Tag) by treating as a query the base sequence of cDNA encoding human MLP precursor protein obtained in EXAMPLE 1 and which was the unique EST considered to contain the 3' region of cDNA encoding mouse MLP precursor protein. 5' RACE was carried out using as an antisense strand primer the oligo DNA shown by SEQ ID NO:7, and 3' RACE was carried out using as a sense strand primer the oligo DNA shown by SEQ ID NO:8, whereby the 5' upstream sequence and the 3' downstream sequence starting from the respective primers were obtained, respectively. Base sequencing of each of the double stranded DNAs obtained indicates the presence of overlapping common sequences, which reveals that the two sequences are derived from the same gene. Therefore, the respective cDNA fragments obtained by 5' RACE and 3' RACE were ligated with the common sequence segment to finally obtain poly(A)$^+$ chain-containing cDNA fragment of 947 base pairs (bp) in the full-length (SEQ ID NO:30). This cDNA fragment encoded a novel mouse MLP precursor protein of 218 amino acids represented by SEQ ID NO:12, containing a typical signal sequence of 18 amino acid residues shown by SEQ ID NO:11, as in human MLP precursor protein. In this mouse MLP precursor protein, the positions of four cysteine residues, which are present in human and mouse MIA precursor proteins and human MLP precursor protein, all coincided (FIG. 1). Also, the homology of mouse MLP precursor protein to human MLP precursor protein reached 84.3% on an amino acid level, and but the homology between mouse MIA precursor protein and mouse MLP precursor protein was only 22.6%.

Plasmid pDRL128vM bearing the DNA encoding mouse MLP precursor protein obtained this EXAMPLE was transfected to *Escherichia coli* XL10-Gold to acquire transformant *Escherichia coli* XL10-Gold/pDRL128vM.

EXAMPLE 3

Expression of MLP in Cartilage Differentiation Model in vitro

Mouse embryonic tumor-derived cell line ATDC5 has been used as an in vitro cartilage differentiation model, since ATDC5 can retain the property of precursor cartilage cells extremely well, can induce cartilage differentiation in a high rate by incubation in the presence of insulin, and can simulate all stages of cartilage differentiation observed in subsequent osteogenesis (Cell Diff. Dev., 30:109–116, 1990, J. Cell Biol., 133:457–468, 1996, J. Bone Min. Res., 10:S234, 1995). Thus, a change in expression of various genes at each stage of the differentiation was monitored by performing RT-PCR according to the procedures below. First, ATDC5 cells collected from each stage of the differentiation model incubation system were lysed in a homogeneous liquid ISOGEN (Nippon Gene Co., Ltd.) containing phenol and guanidine thiocyanate, and chloroform was added to the lysate. By centrifugation, the aqueous fraction containing RNA was acquired and isopropanol was further added thereto. The mixture was agitated, again centrifuged and precipitated to obtain the purified total RNAs. Next, using AMV Reverse Transcriptase XL and Random 9 mers in TAKARA RNA PCR Kit (AMV) Ver. 2.1 (Takara Shuzo Co., Ltd.), each of the total RNAs to be tested was reverse transcribed to obtain cDNAs. Then, using these cDNAs as a template DNA and further using as a housekeeping gene G3 PDH (glyceraldehyde 3-phosphate dehydrogenase)-specific oligo DNA (SEQ ID NO: 13, SEQ ID NO:14), or cartilage differentiation marker gene-specific oligo DNA (aggrecan (SEQ ID NO:15, SEQ ID NO:16), type II collagen (SEQ ID NO:17, SEQ ID NO:18), type X collagen (SEQ ID NO:19, SEQ ID NO:20)) as a primer DNA, PCR was carried out in the reaction system of TaKaRa Ex Taq™ (Takara Shuzo Co., Ltd.). The resulting reaction products were separated by agarose gel electrophoresis and the amounts produced were compared. As the result, the expression patterns shown in TABLE 1 corresponding to the respective differentiation stages of cartilage cells could be detected. Now, using as a primer DNA oligo DNA specific to cDNA encoding mouse MLP precursor protein (SEQ ID NO:21, SEQ ID NO:22) and otherwise under the same reaction conditions, RT-PCR was carried out in the cDNA sample group. The amount of mouse MLP precursor mRNA was markedly increased from stage 2 to stage 4. This reveals that the gene of MLP precursor is of such a nature that its expression increases at the initial stages of cartilage differentiation.

TABLE 1

| STAGE | 1 | 2 | 3 | 4 | 5 | 6 | 7 |
|---|---|---|---|---|---|---|---|
| MLP | + | +++ | +++ | +++ | ++ | ++ | + |
| Aggrecan | + | ++ | ++ | ++ | +++ | ++ | ++ |
| TypeII collagen | + | ++ | +++ | +++ | +++ | ++ | ++ |
| TypeX collagen | + | + | ++ | ++ | +++ | +++ | +++ |
| G3PDH | ++ | ++ | ++ | ++ | ++ | ++ | ++ |

The number of symbol + in the table denotes differences in the amount of each gene expressed in each stage of differentiation; the larger the number, the more the amount expressed.

EXAMPLE 4

Expression of Mouse MLP-FLAG Fused Protein in COS7 Cells and its Detection

In order to verify that MLP is a secretory protein, mouse MLP was examined by the following procedures through expression of mouse MLP-FLAG fused protein in COS7 cells and its detection. First, two primer DNAs were chemically synthesized based on the base sequence of cDNA encoding mouse MLP precursor polypeptide obtained in EXAMPLE 2. One is shown by 5'-CGAATTCCCACC-ATGGCAAGGATATTGATTCTTTTGCTTG-3' (SEQ ID NO:27) and is oligo DNA containing the sense sequence of +1 to +28 (wherein the translation initiation site is made +1) bearing the anchored sequence containing the restriction enzyme EcoRI recognition site at the 5' end. Another is shown by 5'GTACAGTCGACTTCACAGAA-GMGTCAATATCCGTGGTTG-3' SEQ ID NO:28) and is oligo DNA bearing the anchored sequence containing the restriction enzyme SalI recognition site with the antisense sequence of +355 to +378 at the 3' end. Using as a template plasmid pDRL128vM obtained in EXAMPLE 2 and further using these two primer DNAs and TaKaRa LA Taq™ (Takara Shuzo Co., Ltd.), amplification was performed with a thermal cycler GeneAmp™ PCR system 9700 (Perkin-Elmer Inc.), which included first allowing to stand at 98° C. for 30 seconds followed by repeating-25 cycles set to include 98° C. for .10 seconds, 55° C. for 20 seconds and 72° C. for 2 minutes as one cycle. Finally extension was performed at 72° C. for 5 minutes. The DNA fragment thus obtained was purified, truncated with restriction enzymes EcoRI and SalI, and then purified again. The purified product was inserted into and ligated with the EcoRI and SalI sites of expression vector pCAN618FLAG for animal cells. pCAN618FLAG derived from plasmid vector pCAN618 and having a neomycin resistant gene as a selection marker can express a protein of interest under control of very early gene enhancer of cytomegalovirus and β-actin promoter downstream the enhancer, by inserting the DNA fragment encoding the protein of interest into its cloning sites, i.e., the EcoRI and SalI sites. Moreover, pCAN618FLAG is also capable of expressing the protein of interest as a FLAG fused protein, by adjusting its reading frame to the base sequence encoding FLAG epitope sequence of 8 amino acids (Asp-Tyr-Lys-Asp-Asp-Asp-Asp-Lys) located immediately after the SalI site and termination codon. The PCR cloning DNA fragment described above was inserted into pCAN618FLAG for the purpose of expressing the fused protein of the full length mouse MLP precursor and FLAG epitope (one Val residue is inserted therebetween). Thus, expression vector plasmid pMMLP-F was obtained.

Next, $1.2 \times 10^5$ COS7 cells were charged in a 6-well plate and incubated for 24 hours in Dulbecco's Modified Eagle's medium (DMEM) supplemented with 10% fetal bovine serum (FBS), and the expression plasmid pMMLP-F (0.4 μg per well) described above was transfected to the cells using Lipofectamine (Gibco BRL). Twenty four hours after the transfection, the medium was replaced by a fresh DMEM medium and then further 5 hours later by FBS-free Opti-MEM (Gibco BRL). After incubation for 36 hours, the culture supernatant and the cell extract were obtained. The cells in the cell extract were washed twice with phosphate buffered saline (PBS), lysed and extracted with Tris SDS sample buffer solution. On the other hand, the culture supernatant was appropriately concentrated by ultrafiltration (molecular weight 3000 cut off) and the concentrate was mixed with an equal volume of Tris SDS sample buffer solution. These samples were heat-treated and then electrophoresed on 15%–25% SDS-polyacrylamide gel. The protein was again transferred from the gel onto a PVDF membrane (Amersham Pharmacia Biotech Inc.). Next, the PVDF membrane was blocked for an hour with Block Ace (Snow Brand Milk Products Co., Ltd.) followed by reacting for 2 hours with anti-FLAG monoclonal antibody (10 μg/ml; Kodak) in PBS containing 0.05% Tween 20 (PBS-T). After washing three times with PBS-T, the reaction product was reacted in PBS-T for an hour with horseradish peroxidase-labeled anti-mouse IgG goat antibody (Amersham Pharmacia Biotech Inc., 5000-fold dilution). After washing 5 times with PBS-T, chemical light emission was detected using ECLplus color forming kit (Amersham Pharmacia Biotech Inc.) and ECL film (Amersham Pharmacia Biotech Inc.). As the result, the gene product of about 14 kDa was detected both in the cell extract and in the culture supernatant, clearly showing that mouse MLP-FLAG fused protein was expressed and secreted in COS7 cells.

Next, the N-terminal amino acid sequence of the mouse MLP-FLAG fused protein was sequenced. First, affinity chromatography was performed using Anti-FLAG™ M2-Agarose Affinity Gel (Sigma Co.) to collect the acidic eluate fraction (eluted with Glycine-HCl buffer (pH 3.5)) from the culture supernatant of COS7 cells containing mouse MLP-FLAG expressed by a modification of the above method. After the fraction was concentrated, the concentrate was electrophoresed on SDS-polyacrylamide gel as described before in this EXAMPLE, followed by CBB staining. Only a single band corresponding to the protein of interest, i.e., mouse MLP-FLAG was observed. The concentrate sample of the same fraction was subjected to electrophoresis in a similar manner. The protein was transferred from the gel onto PVDF membrane and then applied to a pulse liquid amino acid sequencer Procise CLC491 (PE Biosystems Inc.) to determine the N-terminal amino acid sequence. As the result, the amino acid residues of 1. histidine, 2. glycine, 3. valine and 4. phenylalanine were detected in this order, respectively, from the left hand, to coincide with the N-terminal sequence of mouse MLP represented by SEQ ID NO:26. The foregoing results reveal that in mouse MLP-FLAG protein, the signal sequence of N-terminal 18 amino acid residues in mouse MLP-FLAG precursor protein was cleaved and secreted from COS7 cells into medium as mouse MLP-FLAG mature protein starting with the 19th histidine residue.

EXAMPLE 5

Establishment of Mouse MLP-FLAG Fused Protein-expressing CHL-K1 Cell Line

Mouse MLP-FLAG fused protein-expressing CHL-K1 cell line was established by the following procedures. On a plastic Petri dish of 10 cm in diameter, $3.3 \times 10^4$ CHOI-K1 cells were incubated for 24 hours in F-12 medium (Gibco BRL) supplemented with 10% fetal bovine serum (FBS), and the expression plasmid PMMLP-F (1.5 μg per well) obtained in EXAMPLE 4 was transfected to the cells by the calcium phosphate method (CellPhect Transfection Kit (Amersham Pharmacia Biotech Inc.). Twelve hours after the transfection, the cells were washed twice with FBS-free F-12 medium and subjected to glycerol shock for 3 minutes using 3 ml of isotonic HEPES solution (pH 7.5) containing 15% glycerol. The cells were again washed twice with FBS-free F-12 medium and incubated in F-12 medium supplemented with FBS for further 12 hours. The medium was then replaced by F-12 selection medium supplemented with 500 mg/L Geneticin (Gibco BRL) and 10% FEBS (hereinafter selection medium). Ten days after, Geneticin-resistant colonies formed in the Petri dish were transferred to a 24-well plate, respectively, followed by incubation in selection medium for 3 days. Next, the cells proliferated in the selection medium were transferred to a 6-well plate and incubated in selection medium for further 4 days. The medium was replaced by 1 ml of Opti-MEM (Gibco BRL) supplemented with 0.02% CHAPS and 0.1 mM p-ABSF (Wako Pure Chemical Industries Co., Ltd.). After incubation for further 48 hours, the culture supernatant was recovered. The resulting supernatant was concentrated through Centricon YM-3 ultrafiltration membrane (Amicon Inc.), and the concentrate was mixed with an equal volume of Tris SDS sample buffer solution. The sample was heat-treated at 95° C. for 5 minutes and then electrophoresed on 18% SDS-polyacrylamide gel. The electrophoresed protein was further transferred from the gel onto a nylon membrane. Next, the nylon membrane was blocked for an hour with Block Ace (Snow Brand Milk Products Co., Ltd.) followed by reacting for an hour with anti-FLAG antibody (1/2000 dilution, SIGMA) in PBS containing 0.05% Tween 20 (PBS-T). After washing 5 times with PBS-T, the reaction product was reacted in PBS-T for an hour with HRP-labeled anti-mouse IgG sheep antibody (1/2000 dilution, Amersham-Pharmacia Biotech Inc.). After washing 5 times with PBS-T, chemical light emission was detected using ECL color forming kit (Amersham Pharmacia Biotech Inc.) and Hyperfilm ECL (Amersham Pharmacia Biotech Inc.). As the result, the objective gene product of about 16 kDa was detected in the largest quantity in the culture supernatant of the cells derived from CHO-K1/mMLP.FLAG#2-1 strain. Therefore, the cell line was selected as mouse MLP-FLAG fused protein-expressing CHO-K1 cell line.

EXAMPLE 6

Preparation of MLP Antiserum and Detection of Recombinant MLP Protein Using the Antiserum The anti-MLP antiserum was prepared by the following procedures. First, a synthetic peptide (Val-Lys-Glu-Gln-Arg-Val-Tyr-Gln-Glu-Ala-Thr-Lys-Glu-Ile-Pro-Thr-Thr-Asp-Ile-Asp-Cys)(SEQ ID NO:53) represented by SEQ ID N0:31, which is a peptide chain corresponding to the amino acid sequence from the 105th valine to the 124th aspartic acid in mouse MLP precursor protein further added with one cysteine at the C terminus of the protein, was chemically synthesized by a publicly known method. The synthetic peptide was coupled to KLH (keyhole limpet hemocyanin) as a carrier, and it was injected to rabbit for immunization. After immunization was repeated 7 times in total, whole blood was collected and fractionated by a publicly known method to obtain the serum fraction. Sodium azide as a preservative (final concentration of 0.1% was added to the serum fraction, which was used as anti-MLP antiserum.

Next, the reactivity of the antiserum to various recombinant proteins was examined by Western blot analysis. First, in addition to the mouse MLP-FLAG fused protein described in EXAMPLE 4, the respective expression vector plasmids, i.e., mouse MLP protein (no FLAG tag), human MLP-FLAG fused protein, human MLP protein (no FLAG tag), mouse MIA-FLAG fused protein and mouse MIA protein (no FLAG tag), were constructed. These plasmids were constructed as in EXAMPLE 4, by inserting the previously PCR-cloned DNA fragment of interest into the EcoRI and SalI sites which are the cloning sites of pCAN618FLAG. The respective base sequences of the primer DNA set used for the respective PCR reactions are the base sequences represented, respectively, by SEQ ID NO:27 and SEQ ID NO:32 for mouse MLP protein (no FLAG tag), by SEQ ID NO:33 and SEQ ID NO:34 for human MLP-FLAG fused protein, by SEQ ID NO:33 and SEQ ID NO:35 for human MLP protein (no FLAG tag), by SEQ ID NO:36 and SEQ ID NO:37 for mouse MIA-FLAG fused protein and by SEQ ID NO:36 and SEQ ID NO:38 for mouse MIA protein (no FLAG tag). As a template DNA, there was used, respectively, pDRL128vM for mouse MLP protein (no FLAG tag) as in EXAMPLE 4, pDRL128vH obtained in EXAMPLE 1 for human MLP-FLAG fused protein and human MLP protein (no FLAG tag), and cDNA prepared from mouse melanoma cell line B16 for mouse MIA-FLAG fused protein and mouse MIA protein (no FLAG tag). Transfection of the respective expression vector plasmids thus obtained to COS-7 cells and the Western blot analysis on the respective culture supernatants using anti-FLAG antibody were performed in a manner similar to the procedures of EXAMPLE 4. The Western blot analysis using the anti-MLP antiserum was performed in a similar manner to the procedures of the Western blot analysis using the anti-FLAG antibody, except that the antiserum (1000-fold dilution) was used as a primary antibody and as a secondary antibody, horseradish peroxidase labeled anti-rabbit IgG antibody (Amersham Pharmacia Biotech; 5000-fold dilution) was used.

Figure 2:
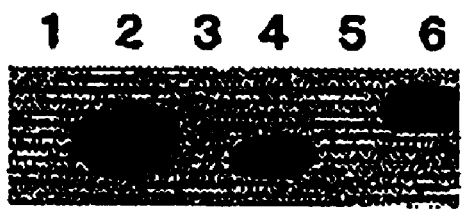
FIG. 2 shows the results of Western blotting analysis performed in EXAMPLE 6, in which anti-FLAG antibody was employed as a primary antibody.

FIG. 2 shows the results of the Western blot analysis using the anti-FLAG antibody and FIG. 3 shows the results of the Western blot analysis using the anti-MLP antibody. The anti-MLP antiserum showed cross reactivity with both mouse MLP and human MLP, which are antigen peptide-derived proteins, and the reactivity was almost the same. Also, mouse MLP-FLAG fused protein and human MLP-FLAG fused protein were reacted with the antiserum, indicating that it was not affected even in the presence of FLAG tag. On the other hand, no signal was detected at all with mouse MIA-FLAG fused protein or mouse MIA protein (no FLAG tag), and the results reveal that the antiserum was specific to the MLP molecular species.

Furthermore, the mouse MLP-FLAG expressing CHO cell line acquired in EXAMPLE 5 using the antiserum was subjected to immune staining by a modification of publicly known methods. The results are shown in FIG. 4. In the control experiment using rabbit serum prior to immunization, each cell was not stained but all cells were stained when the antiserum was used. This reveals that the antiserum was also reactive with denatured MLP protein.

EXAMPLE 7

Expression of MLP Protein in Cartilage Tissue

Using the anti-MLP antiserum obtained in EXAMPLE 6, it was attempted to detect MLP protein in the cartilage tissue. As a test specimen, mouse (BALB/c) femoral head cartilage was used after freeze-destructing with liquid nitrogen, extracting with TRIS SDS β ME SAMPLE BUFFER (Daiichi Kagaku Yakuhin K. K.) and removing the residue by centrifugation. A sample in an amount corresponding to that derived from one mouse per lane was electrophoresed on SDS-PAGE (15–25%) followed by Western blot analysis using anti-MLP antiserum as in EXAMPLE 6. The results reveal that since a signal was detected at almost the same electrophoretic position as in mouse MLP recombinant protein, MLP protein was expressed in the cartilage tissue.

In order to examine expression of human MLP mRNA in various human tissues other than the cartilage tissue, a probe was prepared by the method of Multiprime DNA labeling'system (Amersham Pharmacia Biotech: RPN. 1601Y) using the DNA fragment encoding the human MLP precursor protein obtained in EXAMPLE 1 and [$\alpha$-$^{32}$ P] dCTP (Amersham Pharmacia Biotech: Ci/mmol), and hybridization with Human MTE™ Array (CLONTECH Inc.: #7775-1) was performed using the probe (specific activity of 1.3×1010 cpm/μg). The hybridization was carried out under the conditions according to the manual attached to the array membrane. The final washing was conducted with 0.1×SSC and 0.1% SDS at 55° C. and detection was made using BAS-2000 (Fuji Photo Film Co., Ltd.). As the result, signals observed on the array were human chromosomal DNA for control (100 ng, 500 ng) and only trace'spots of nigra and fetal brain, but any of the signals was around the detection limit. It was thus judged that the amount of expression was extremely low at the transcription stage. Therefore, it was strongly suggested that MLP protein would be specifically expressed in the cartilage tissue.

EXAMPLE 8

Effect of adding MLP recombinant protein on change in expression of various genes in the cartilage differentiation model in vitro In the cartilage differentiation model in vitro using the ATDC5 cells described in EXAMPLE 3, the effect of adding MLP recombinant protein on change in expression of various genes was examined. The MLP recombinant protein obtained as in EXAMPLE 4 by performing affinity chromatography according to a publicly known method using anti-FLAG antibody and purifying/concentrating from the culture supernatant of mouse MLP-FLAG fused protein-expressed COS-7 cells, was used as a specimen. The protein was added to ATDC5 cells every two other days from the first day when the model system was set, followed by incubation for 10 days. The cells were then recovered, and expression of each gene was examined by RT-PCR as in EXAMPLE 3. As the result, suppressed expression of each marker gene showing the increased amount of expression with differentiation, such as aggrecan, type II collagen, type X collagen, etc. was noted in the protein-added cell group. On the other hand, any significant affect was not noted with change in expression of PTH/PTHr receptor that acts suppressively on differentiation of cartilage. This result reveals that MLP protein acts suppressively on cartilage differentiation in this model system using ATDC5.

EXAMPLE 9

Aynalisys of Gene Encoding Rat MLP Precursor Protein (rMLP)

First, the DNA fragment encoding a part of rMLP was obtained by the following PCR procedures. That is, 20 μl of a solution mixture containing 4 pmol each of oligo DNA shown by SEQ ID NO:21 as a sense strand primer and oligo DNA shown by SEQ ID NO:22 as an antisense strand primer, further containing 2 µl of 10×Advantage™ 2 PCR Buffer (Clonetech Inc.), 0.4 µl of 50×dNTP mix (Clonetech Inc.), 0.4 µl of 50×Advantage 2 Polymerase Mix (Clonetech Inc.) and 2 µl of a solution of SD(IGS) rat pituitary-derived cDNA as a template DNA was prepared. Using a thermal cycler (GeneAmp™ PCR sytem model 9700 (Perkin-Elmer, Inc.)), PCR was carried out according to the program which comprises treating at 95° C. for a minute, repeating 35 cycles set to include 95° C. for 10 seconds, then 54° C. for 10 seconds and 72° C. for a minute, and then performing extension at 72° C. for 3 minutes. After completion of the reaction, the solution was subjected to electrophoresis using 2.0% agarose gel, and the gel was stained with SYBR™ Green I nucleic acid gel stain (Molecular Sieve Inc.). It was confirmed that a band corresponding to DNA amplified by PCR was found at the position of about 300 bp when converted on the molecular weight marker. The DNA fragment was recovered using QIAquick Gel Extraction Kit (Qiagen), and subjected to TA cloning using pCR™ 2.1-Topo (Invitrogen Inc.) to determine its base sequence. The plasmid was transfected to competent cells of *Escherichia coli Epicurian Coli* XL10-Gold™ strain (Stratagene Co.). A clone bearing the foreign DNA fragment-inserted plasmid was selected from colonies of ampicillin-resistant transformants appeared on an ampicillin-containing LB agar medium, and the plasmid DNA, pDRL128vR, was prepared from the clone. In order to determine the base sequence of the inserted DNA, sequencing using ABI PRISM™ BigDye Terminator Cycle Sequencing FS Ready Reaction Kit (Perkin-Elmer, Inc.) was carried out by a thermal cycler (GeneAmp™ PCR system model 9700 (Perkin-Elmer, Inc.)) under the conditions according to the brochure attached, using pDRL128vR as a template DNA and commercially available DNA (Bca BEST Primer RV-P (Takara Shuzo Co., Ltd.)) as a sequencing primer. Thereafter, the reaction sample was analyzed by a DNA sequencer ABI PRISMT™ 377 (Perkin-Elmer, Inc.).

Thus, the DNA fragment of 307 base pairs shown by SEQ ID NO:41 containing the DNA fragment of 261 base pairs shown by SEQ ID NO:40 encoding a part of novel rat MLP precursor protein of 87 aminoacids shown by SEQ ID NO:39 was contained in pDRL128vR.

Turning next to the gene encoding the protein, genome walking was performed to examine the structure more upstream the 5' end and more downstream the 3' end than the base sequence above. As a test material, Rat GenomeWalker™ Kit. (Clonetech Inc.) was used, and the procedures were carried out according to the protocol attached to the kit, except for using TaKaRa Ex Taq™ (Takara Shuzo Co., Ltd.) as an enzyme for PCR. First, two oligo DNAs (rMLPGWF1 (SEQ ID NO:42) and rMLPOWF2 (SEQ ID NO:43)) corresponding to a part of the base sequence shown by SEQ ID NO:40 and two oligo DNAs (rMLPGWR1 (SEQ ID NO:44) and rMLPGWR2 (SEQ ID NO:45)) complimentary to a part of the base sequence above were chemically synthesized, respectively, as gene specific primers. As the primers, rMLPGWF1 was used in the first PCR reaction for acquiring the 3' downstream DNA, and in the following nested PCR, rMLPGWF2 was employed. In the first PCR for acquiring the 5' upstream DNA, rMLPGWR1 was used and, rMLPGWR2 was used in the following nested PCR. As to the amplified DNA fragments obtained by these reactions, the respective base sequences were analyzed, while making comparison in homology to the base sequences of cDNAs encoding human and mouse MLP precursor proteins, based on the above primer sequence sites as the start. As the result, it has become clear from the identified primary structure of genome that rat MLP precursor protein is a protein composed of 128 amino acid residues represented by SEQ ID NO:47 encoded by DNA of 384 bases shown by SEQ ID NO:46. The homology of rat MLP precursor protein to human MLP precursor protein and mouse MLP precursor protein on an amino acid level reached 84.3% and 96.0%, respectively, but the homology of rat MIA precursor protein to rat MLP precursor protein was only 26.5%. Rat MLP is a protein composed of 110 amino acid residues represented by SEQ ID NO:49 encoded by DNA of 330 bases represented by SEQ ID NO:48, and it is considered that a signal peptide composed of 18 amino acids as in mouse MLP, represented by SEQ ID NO:50, would be processed and produced from rat MLP precursor protein.

Plasmid pDRL128vR bearing the DNA encoding a part of rat MLP precursor protein obtained in this EXAMPLE was transfected into *Escherichia coli* XL10-Gold to obtain transformant, *Escherichia coli* XL10-Gold/pDRL128vR.

Industrial Applicability

The polypeptide of the present invention and DNA encoding the same can be used for the diagnosis, treatment, prevention, etc. of, e.g., bone and joint diseases and pathological angiogenesis. Further, the polypeptide of the present invention is useful as a reagent for screening a compound or its salt that promotes or inhibits the activity of the polypeptide of the present invention. Furthermore, the antibody to the polypeptide of the present invention is capable of recognizing the polypeptide of the present invention specifically and can thus be used for the detection, quantification, neutralization, etc. of the polypeptide of the present invention in a test sample fluid.

Further by using the promoter of the present invention, a large quantity of a protein (an optional useful gene product, etc.) can be expressed predominantly in the cartilage of non-human warm-blooded animal and hence, can contribute to the field of gene therapy.

What is claimed is:

1. An isolated polypeptide comprising the amino acid sequence represented by SEQ ID NO:24; or its amide or ester, or a salt thereof.

2. The polypeptide, its amide or ester, or a salt thereof, according to claim, 1, which consists of the amino acid sequence represented by SEQ ID NO:6.

3. An isolated polypeptide or its amide or ester, or a salt thereof, which comprises the amino acid sequence represented by SEQ ID NO:26.

4. The polypeptide or its amide or ester, or a salt thereof, according to claim 3, which consists of the amino acid sequence represented by SEQ ID NO:12.

5. An isolated polypeptide or its amide or ester, or a salt thereof, which comprises the amino acid sequence represented by SEQ ID NO:49.

6. The polypeptide or its amide or ester, or a salt thereof, according to claim 5, which consists of the amino acid sequence represented by SEQ ID NO:47.

7. An isolated nucleic acid comprising a nucleic acid sequence encoding the polypeptide comprising the amino acid sequence represented by SEQ ID NO:6, 12, 24, 26, 47 or 49.

8. The isolated nucleic acid according to claim 7, wherein the nucleic acid sequence is represented by SEQ ID NO:23.

9. The isolated nucleic acid according to claim 7, wherein the nucleic acid sequence is represented by SEQ ID NO:4.

10. The isolated nucleic acid according to claim 7, wherein the nucleic acid sequence is represented by SEQ ID NO:25.

11. The isolated nucleic acid according to claim 7, wherein the nucleic acid sequence is the represented by SEQ ID NO:10.

12. The isolated nucleic acid according to claim 7, wherein the nucleic acid sequence is represented by SEQ ID NO:48.

13. The isolated nucleic acid according to claim 7, wherein the sequence is represented by SEQ ID NO:46.

14. A composition comprising the polypeptide, its amide or ester, or a salt thereof, which comprises the amino acid sequence represented by SEQ ID NO:6, 12, 24, 26, 47 or 49 and a pharmaceutical carrier.

15. An isolated polypeptide wherein the polypeptide comprises an amino acid sequence selected from the group consisting of SEQ ID NO. 6, 12, 24, 26, 47 and 49.

16. A recombinant vector comprising the nucleic acid according to claim 7.

17. A transformant transformed with the recombinant vector according to claim 16.

18. A method for manufacturing the polypeptide comprising the amino acid sequence represented by SEQ ID NO:6, 12, 24, 26, 47 or 49, which comprises culturing a transformant transformed with the recombinant vector comprising a nucleic acid sequence encoding the polypeptide, and producing the polypeptide.

* * * * *